(12) United States Patent
Chan et al.

(10) Patent No.: US 10,546,656 B2
(45) Date of Patent: Jan. 28, 2020

(54) BIOPSY MAPPING TOOLS

(71) Applicant: Acupath Laboratories, Inc., Plainview, NY (US)

(72) Inventors: Kee Chan, Hicksville, NY (US); Minning Xie, Bethpage, NY (US); Barbara Winter, East Norwich, NY (US); Larry Fox, Lawrence, NY (US)

(73) Assignee: Acupath Laboratories, Inc., Plainview, NY (US)

( * ) Notice: Subject to any disclaimer, the term of this patent is extended or adjusted under 35 U.S.C. 154(b) by 0 days.

(21) Appl. No.: 16/403,715

(22) Filed: May 6, 2019

(65) Prior Publication Data

US 2019/0259481 A1   Aug. 22, 2019

Related U.S. Application Data

(62) Division of application No. 14/707,902, filed on May 8, 2015, now Pat. No. 10,340,041.

(60) Provisional application No. 61/990,844, filed on May 9, 2014.

(51) Int. Cl.
| | |
|---|---|
| *G16H 15/00* | (2018.01) |
| *G06F 16/2457* | (2019.01) |
| *G06F 16/248* | (2019.01) |
| *G16H 10/60* | (2018.01) |
| *G06F 16/50* | (2019.01) |

(52) U.S. Cl.
CPC .......... *G16H 15/00* (2018.01); *G06F 16/248* (2019.01); *G06F 16/24575* (2019.01); *G06F 16/24578* (2019.01); *G06F 16/50* (2019.01); *G16H 10/60* (2018.01)

(58) Field of Classification Search
USPC .......................................... 382/128; 705/2–3
See application file for complete search history.

(56) References Cited

U.S. PATENT DOCUMENTS

| | | | | |
|---|---|---|---|---|
| 4,654,701 | A * | 3/1987 | Yabe ...................... | A61B 10/00 348/74 |
| 5,991,729 | A * | 11/1999 | Barry ..................... | G06Q 50/22 705/3 |
| 6,678,397 | B1 * | 1/2004 | Ohmori .................. | G06F 16/10 382/128 |
| 8,700,432 | B2 * | 4/2014 | Letts ..................... | G06F 19/321 705/2 |
| 10,340,041 | B2 * | 7/2019 | Chan .................. | G06F 16/24575 |

(Continued)

*Primary Examiner* — Ishrat I Sherali
(74) *Attorney, Agent, or Firm* — Weiss & Arons LLP

(57) ABSTRACT

Apparatus for plotting pathological diagnoses on anatomical diagrams is provided. The apparatus may include a mapping tool. The mapping tool may identify a plurality of biopsy marker records including a received criterion. The mapping tool may identify a body part image associated with a body part image ID. The mapping tool may section the body part image into a first quadrant and a second quadrant. The mapping tool may loop through the plurality of biopsy marker records to identify an X,Y coordinate associated with each of the plurality of biopsy marker records. For each X,Y coordinate identifying a location within the first quadrant, the mapping tool may iteratively tally a first count for the first quadrant. For each X,Y coordinate identifying a location within the second quadrant, the mapping tool may iteratively tally a second count for the second quadrant.

21 Claims, 26 Drawing Sheets

(56) References Cited

U.S. PATENT DOCUMENTS

| | | | |
|---|---|---|---|
| 2007/0260488 A1* | 11/2007 | Heywang-Kobrunner | ..................  G06F 19/321  705/2 |
| 2010/0257214 A1* | 10/2010 | Bessette | ................. G16H 10/60  707/812 |
| 2015/0051916 A1* | 2/2015 | Vdovjak | ............ G06Q 10/0631  705/2 |
| 2015/0097868 A1* | 4/2015 | Banerjee | ............... G06F 19/321  345/634 |
| 2016/0012319 A1* | 1/2016 | Mabotuwana | ........ G06F 19/321  382/128 |
| 2016/0085913 A1* | 3/2016 | Evans | .................... A61B 10/00  705/3 |
| 2017/0076046 A1* | 3/2017 | Barnes | .................. G06F 19/321 |
| 2018/0267700 A1* | 9/2018 | Kaditz | ................ G06F 3/04847 |

\* cited by examiner

| BATCH: # | DERMATOPATHOLOGY REPORT | | | NHC: STPL 1 OF 1 |
|---|---|---|---|---|
| | SPECIMEN | A | B | C |
| | PANEL REPORT DATE | 04/13/XX | 04/13/XX | 04/13/XX |
| | SUBMITTED: 3 VIALS-A,B,C | | | |

401

OBTAINED: 06/11/20XX
RECEIVED: 06/12/20XX   5:28 pm

PATIENT: JACK S. JONES
12345 ANYWHERE STREET
NEW YORK, NY 10013
(212) 555-1111          ACCT # : 12345
DOB: 03/17/19XX         AGE: 46
                        SEX: MALE

ABC SURGERY CENTER
PHYSICIAN: JOHN SMITH
12345 FIRST AVE, SUITE 8A
NEW YORK, NY 10018      (212) XXX-XXXX
Acct # XXX-XXX-XXX      (212) XXX-XXXX

403

DIAGNOSIS

A ● LT CHEST
DIAGNOSIS; BASAL CELL CARCINOMA, SUPERFICIAL TYPE
NOTES: THE MARGINS ARE FREE OF LESION IN THE PLANES OF SECTION EXAMINED.
MICROSCOPIC DESCRIPTION : SECTIONS SHOW A NEOPLASM EXTENDING FROM THE EPIDERMIS INTO THE SUPERFICIAL DERMIS, COMPOSED OF BUDS OF CELLS WITH RELATIVELY UNIFORM HYPER CHROMATIC NUCLEI SCANTY CYTOPLASM AND PERIPHERAL PALISADING.
GROSSING INFORMATION: RECEIVED IN 10% FORMALIN IS A SPECIMEN MEASURING 03X02X01MM, COLOR IS TAN, SHAPE IS FLAT AND SUBMITTED IN 1 BLOCK, 1 PIECE.
CLINICAL IMPRESSION: R/O BCC.

405

B ● LT SHOULDER
DIAGNOSIS: BASAL CELL CARCINOMA, PIGMENTED
NOTES: THE MARGINS ARE FREE OF LESION IN THE PLANES OF SECTION EXAMINED, HOWEVER, BASAL CELL CARCINOMA CLOSELY APPROACHES THE BASE OF THE BIOPSY.
MICROSCOPIC DESCRIPTION: THERE IS A DERMA NEOPLASM COMPOSED OF BASALOID CELLS WITH RELATIVELY UNIFORM HYPERCHROMATIC NUCLEI AND SCANTY CYTOPLASM. THE BASALOID CELLS ARE ARRANGED IN LOBULES WITH PERIPHERAL PALISADING . THERE IS MELANIN PIGMENT WITHIN TUMOR CELLS AND / OR SURROUNDING STROMA.
GROSSING INFORMATION: RECEIVED IN 10% FORMALIN IS A SPECIMEN MEASURING 04X02X01 MM, COLOR IS FLAT AND SUBMITTED IN  1BLOCK, 1PIECE.
CLINICAL IMPRESSION R/O BCC.

C● STERNUM
DIAGNOSIS: BASAL CELL CARCINOMA, SUPERFICIAL TYPE
NOTES: THE LESION EXTENDS TO A LATERAL MARGIN.
MICROSCOPIC DESCRIPTION: SECTIONS SHOW A NEOPLASM EXTENDING FROM THE EPIDERMIS INTO THE SUPERFICIAL DERMIS, COMPOSED OF BUDS OF CELLS WITH RELATIVELY UNIFORM HYPERCHROMATIC NUCLEI SCANTY CYTOPLASM AND PERIPHERAL PALISADING.
GROSSING INFORMATION: RECEIVED IN 10% FORMALIN IS A SPECIMEN MEASURING 04X02X01 MM, COLOR IS TAN, SHAPE IS FLAT AND SUBMITTED IN 1 BLOCK, 1 PIECE.
CLINICAL IMPRESSION: R/O BCC.

Photomicrograph:

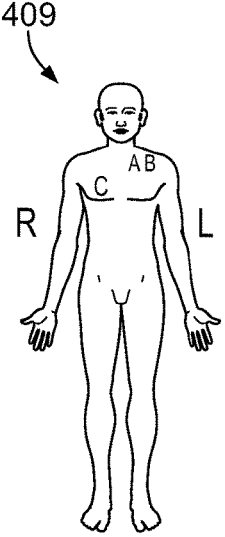
409

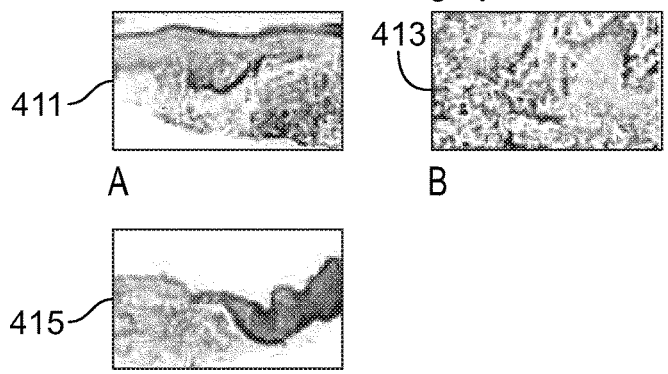
411 — A
413 — B
415 — C

Color Keys  417

- ● CANCER
- △ PRECANCER/DYSPLASIA
- ▦ BENIGN
- ◆ INFECTIONS
- ⊛ INFLAMMATORY
- ⊘ SUSPICIOUS
- ◈ OTHER
- ▨ ATYPICAL

FIG. 4B

BIOPSY MAPPING TOOLS

PRIORITY DATA

This application is a divisional of U.S. patent application Ser. No. 14/707,902, filed on May 8, 2015, which is a nonprovisional of U.S. Provisional Application No. 61/990,844, filed on May 9, 2014, all of which are hereby incorporated herein by reference in its entirety their entireties.

FIELD OF TECHNOLOGY

This invention relates to apparatus and methods for plotting pathological diagnoses on anatomical diagrams. The apparatus includes a mapping tool. The mapping tool may retrieve one or more electronic records. The mapping tool may use the electronic records to generate an anatomical diagram including a symbol associated with a pathological diagnosis.

BACKGROUND OF THE DISCLOSURE

Typical pathology lab reports describe, in words, a location of a biopsy sample (or other clinical finding or test result) and related information such a diagnosis and treatment. If two or more biopsies are taken on different calendar dates, separate lab reports are usually generated for each biopsy.

This is not desirable at least because a health professional is required sift through the text of the report, and sometimes the text of multiple reports, to become familiar with a patient's medical history. It also may be difficult for a report reader to conceptualize a special relationship among various diagnoses from different time periods and associated with different locations on a patient's body.

It is desirable, therefore, to provide systems and methods for displaying pathology or clinical data in an interactive format that allows a user to view, at a glance, multiple medical events for one or more patients. This is desirable at least because viewing medical data collected over time provides a quick, accurate and understandable perspective on the collected data.

For example, a typical pathology lab report may describe, in words, a location of a biopsy sample and related biopsy information such a diagnosis and treatment. If two or more biopsies are taken on different calendar dates, separate lab reports are usually generated for each biopsy.

It may be difficult for readers of the lab reports to correlate the text of the lab report to locations on a patient's body referred to in the lab report text. A reader of the lab report may misread or misunderstand text included in the lab report. A reader of the lab report may be unable to locate, on the patient's body, a location referred to in the text of the lab report.

It would be desirable to present medical information such as clinical findings, lab report or test results in a visual format. A visual format may allow a viewer of the visual report to easily conceptualize diagnoses and locations referenced in the medical information. For example, a visual report of laboratory diagnostic information may allow a viewer of the visual report to more easily associate contents (such as diagnoses) of the visual report to locations on a patient's body.

Additionally, a visual report may include an overlay, on a body part image, of historical lab reports associated with a patient over a period of time. A visual display of the historical lab reports may allow a viewer of the lab reports to quickly, accurately and easily understand a patient's clinical history.

Effective Apr. 7, 2014, a new federal ruling issued by the Centers for Medicare Medicaid Services (Federal Register Number: 2014-02280) now allows patients to access their test results directly from the laboratories in which their testing was performed. Current lab reports are not suited for the general public to understand quickly and accurately.

It is further desirable, therefore, to provide systems and methods for enabling patients, without prior medical training, to view their pathological history and diagnoses superimposed on a diagram that displays an image of a body part. This is desirable at least because such diagrams are easy to understand and allow patients to immediately verify that their biopsies were taken from the correct parts of their bodies, enhancing patient satisfaction and security. Visual display of medical information may also allow a viewer to see a spatial relationship among various diagnoses or clinical findings associated one or more body locations.

SUMMARY OF THE DISCLOSURE

Apparatus and methods for plotting pathological diagnoses on one or more anatomical diagrams are provided. Methods may include receiving an electronic communication containing an accession number. An accession number may be a chart number or other identifier associated with a patient's medical records. Methods may also include running a first query to return, from a database, a plurality of biopsy marker records that include the accession number. Each biopsy marker record may include medical information associated with a clinical assessment of a patient. The medical information may include a clinical assessment associated with a body surface, such as a result of a biopsy taken from the patient's skin. The medical information may include a clinical assessment associated with an internal organ of the body, such as a blood test or a liver biopsy. In response to receiving the plurality of biopsy marker records, the methods may further include running a second query to return a body part image ID associated with the plurality of biopsy marker records. The methods may also include retrieving a body part image associated with the body part image ID.

Methods may further include iterating through the plurality of biopsy marker records to identify an overlapping X,Y coordinate associated with two or more of the plurality of biopsy marker records. Methods may also include identifying a subset of biopsy marker records, each of the biopsy marker records included in the subset being associated with the overlapping X,Y coordinate. Methods may additionally include iterating through the subset to identify a pathological diagnosis associated with each of the biopsy marker records included in the subset.

Methods may further include querying an electronic record storing a hierarchy of pathological diagnoses and, based on the hierarchy, identifying an optimized pathological diagnosis associated with each of the biopsy marker records included in the subset. The optimized diagnosis may identify the most serious diagnosis associated with the subset. Methods may also include generating a display on a graphical user interface ("GUI"), the display including at least a first symbol and a second symbol overlaid on the body part image.

The first symbol may be associated with a first pathological diagnosis. The first pathological diagnosis may be included in a biopsy marker record that is not part of the subset. The second symbol may be associated with the optimized pathological diagnosis. The second symbol may be representative of the at least two biopsy marker records included in the subset.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which:

FIGS. 4A-4B shows yet another illustrative graphical user interface for use with the systems and methods of the invention;

DETAILED DESCRIPTION OF THE DISCLOSURE

Figure 1:
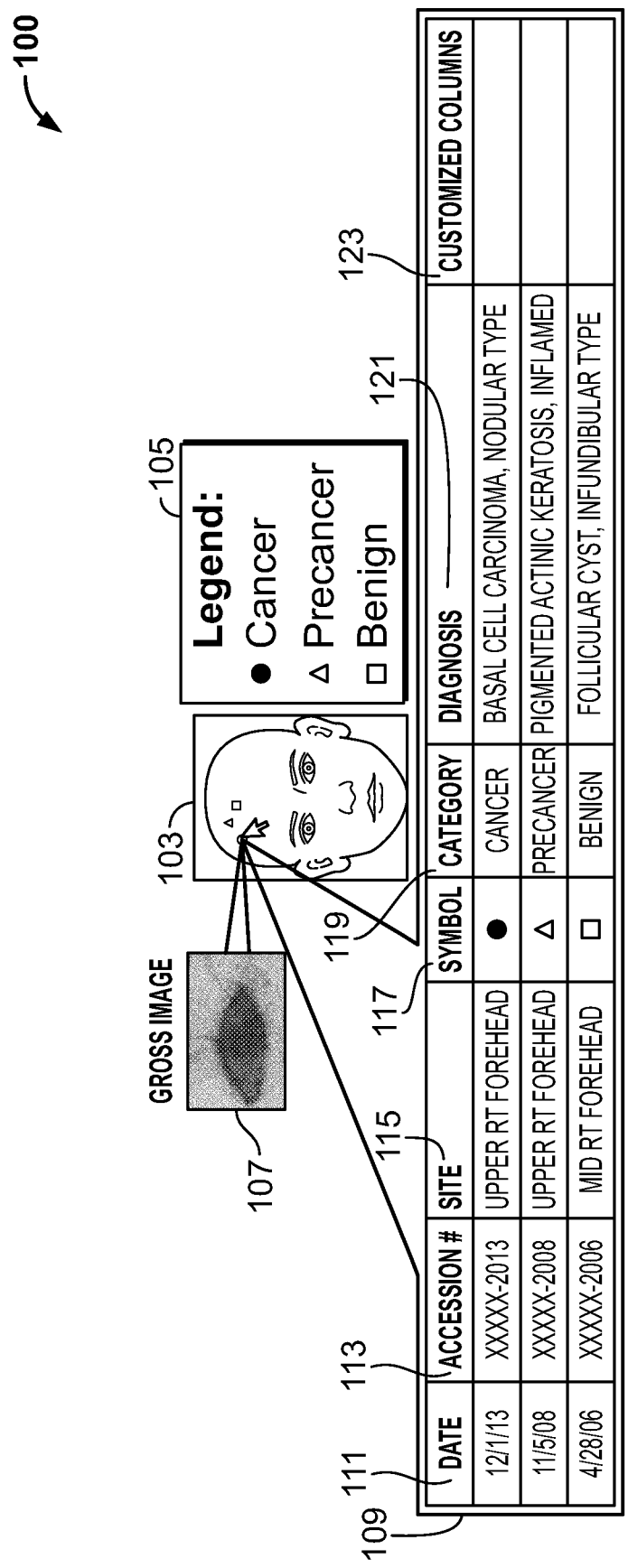
FIG. 1 shows an illustrative graphical user interface for use with the systems and methods of the invention.

Apparatus and methods for a mapping tool are provided. The mapping tool may use historical data stored in electronic records and/or one or more databases to plot medical information on one or more anatomical diagrams. An electronic record may include any suitable medical data for a patient, detailing one or more diagnoses, clinical findings, medical tests, procedures, illnesses, historical records, or any other suitable medical data. In some embodiments, an electronic record may include biopsy information.

The mapping tool may be used by one or more physicians, private practices, group practices, hospitals, laboratories, pharmaceutical companies, healthcare researchers, military hospitals, government agencies, private and government-funded insurance providers or any other suitable users.

In some embodiments, the mapping tool may access the electronic medical records ("EMRs") of patients of the mapping tool's users. An electronic medical record may be a digital patient medical record used by a health care facility to store and update patient medical information.

In some embodiments, the mapping tool may be used by a first user of the tool to transmit medical data, such as EMRs or other data, to a second user of the tool. In some embodiments, the mapping tool may function as a central data repository of data for two or more users of the tool. Data stored by a first user of the mapping tool may be accessed by a second user of the mapping tool, or may be accessibly only to the first user.

The mapping tool may store historical information, which may include historical medical information, in one or more databases. The data may be input into the mapping tool by one or more users of the tool. Additionally, or alternatively, the mapping tool may source, receive, pull or search data from one or more of user databases or from any data repository storing medical information for a population or any other suitable data.

The mapping tool may incorporate a patient's stored historical data with an EMR associated with the patient, or store the patient's historical data across one or more databases. The mapping tool may use the at least some of a patient's data to create one or more electronic records for the patient. An electronic record may be used to store data relating to a medical event in the patient's history. Electronic records created by the mapping tool may be used to generate one or more repots. A report may include one or more images. A report may be integrated into the patient's EMR. A report may assist a physician, or other view of the report, to visually review a portion of a patient's medical information quickly and accurately.

The mapping tool may generate an electronic display of medical information. The mapping tool may generate display of medical information on paper.

For example, in the practice of pathology, a laboratory or physician may take a biopsy sample from an area of the human body. The area of the human body may include a lesion. A user of the mapping tool may input historical data into the mapping tool relating to the patient, the biopsy, the location of the lesion, and a pathological diagnosis associated with the biopsy. Alternatively, the mapping tool may receive and store the historical data in one or more databases. The mapping tool may use at least a portion of the historical data to create an electronic record for the patient. An electronic record including biopsy information may be referred to alternately herein as a "biopsy marker record."

The apparatus and methods of the invention are described below in the context of biopsy data. Any other suitable medical data is included within the scope of the invention. Other illustrative medical information may include clinical finding, such as a skin lesion that should be observed during future visits, a body landmark, blood tests or radiology reports.

Exemplary historical data stored by the mapping tool for the patient includes a numeric patient identifier, the patient's social security number and the patient's date of birth, and a case or accession number. In some embodiments the mapping tool may receive the numeric patient identifier and biopsy information, and issue a case or accession number. The accession number may be a chart number or other unique identifier associated with a patient's medical information. The mapping tool may associate the patient's historical data with the accession number.

Additional exemplary historical data accessible by the mapping tool for a patient may include information identifying where on the human body the lesion was found. The mapping tool may use this information to identify a location on a body part image stored in a body part image database. The identified location may correspond to the area of the human body where the patient's biopsy was found.

The body part image database may include a plurality of body part images. A body part image may be an image of the human body. The body part image may be in 2D or 3D. The images may display an internal portion of the body, an external portion of the body, or the whole human body. Each body part image may be associated with a body part image ID.

In some embodiments, the mapping tool may store a location on a body part image as an X,Y coordinate or an X,Y,Z coordinate, and in some embodiments additional coordinates for three or more dimensional mapping and other features such as image rotation. The coordinates may identify a location on the body part image. The coordinates may identify a location within a body organ. In other embodiments, the mapping tool may store the location associated with the biopsy as a two-dimensional area defined by X,Y coordinates. The two-dimensional area may identify an area located on a body part image. In some embodiments, the mapping tool may store information identifying a three-dimensional area using X,Y,Z coordinates on the body part image from which the biopsy was taken.

In some embodiments, a user may input location data into the mapping tool by generating a display of a selected body part image and identifying, using a touch screen or a mouse, the location on the body part image where the biopsy was taken. For example, by clicking on a portion of displayed image, a clinician may thereby identify a location of a suspicious lesion or other clinical finding. The identified location may be displayed on a body part image to the clinician when the patient returns for a follow-up visit. In yet other embodiments, the mapping tool may receive text describing the body location where the biopsy was taken. The mapping tool may use the text to identify the body part image and a location on the body part image where the biopsy was taken from.

In other embodiments, an electronic diagram including an image of a body part and a marker identifying the location of the biopsy may be electronically transmitted to the mapping tool. The image may be a diagram of at least a portion of the body that is different from the body part images stored in the mapping tool's database(s). The mapping tool may use superimposition mapping techniques to fuse the image with an image stored in the mapping tool's database and identify the location of the biopsy.

In yet other embodiments, the mapping tool may receive a photograph or image of at least a portion of the patient. Exemplary photographs/images may be a photograph of a patient, two/three dimensional diagram identifying one or more biopsy locations such as results from an MRI scan, blood test and/or any other suitable clinical information. The photograph may include a marking on the skin where a biopsy will be taken/has been taken. The mapping tool may use superimposition mapping techniques to correlate the photograph/image with a body part image and map the marking on the skin onto a location of the body part image.

Exemplary superimposition mapping techniques used by the mapping tool may include image recognition and photo fusion. The image recognition may comprise correlating the body part displayed in the photograph/image with a body part image in the mapping tool's database. Once the body part image is identified, the technique may include identifying, on the photograph/image, one or more "match points." Each body part image may have designated match points. For example, for the face, exemplary match points may include top of the forehead, bottom of chin, nose, two sides of mouth.

After identification of the match points, the mapping tool may use the match points to center the mapping tool's body part image over the photograph/image. After the body part image is centered on the photograph/image, a lesion point or biopsy may be identified in the photograph/image. The identified lesion point or biopsy may be mapped onto the body part image. The mapping tool may then assign a location to the lesion point or biopsy, the location identifying the area on the body point image where the lesion point or biopsy is found.

Additional historical data that may be input into the mapping tool includes patient demographics, clinical history and data of the patient provided by the physician, type of biopsy, depth of lesion, biopsy adequacy, biopsy methods, diagnostic testing, biopsy diagnosis, diagnostic category, diagnostic grading, tumor aggressiveness, recurrence rates, cure rates, treatments, treatment modalities, clinical impressions, detailed notes and patient insurance, payment information, discordance or concordance rates between diagnoses by pathologist/healthcare institution/technique, second opinion analyses, quality assurance analyses, insurance payments for insured/uninsured/indigent patients and various types of healthcare-related cost analyses. It should be noted that any other suitable historical data may be input into the mapping tool.

The mapping tool may store one or more pieces of patient historical data detailed above in a new biopsy marker record or an existing biopsy marker record. The mapping tool may use biopsy marker records to generate one or more repots. The reports may be displayed on a GUI.

An exemplary report generated for a patient's biopsy may display a body part image and a symbol. The body part image may be associated with a body part image ID stored in a biopsy marker. The body part image may be a visual image of the area on the human body from which the biopsy was taken. The symbol may be overlaid on the body part image at a location identified in the record. The location may visually represent where on the human body the biopsy was taken from. The symbol may visually identify a diagnosis of the biopsy.

The mapping tool may select a symbol to be overlaid on a body part image based on diagnosis data associated with a biopsy. In some embodiments, each biopsy stored in a biopsy marker record may be associated with a diagnosis. The mapping tool may include a symbol record. The symbol record may include a plurality of diagnoses and a symbol associated with each diagnoses. For each biopsy identified, the mapping tool may identify the associated diagnosis and search the symbol record to identify a symbol associated with the diagnosis. The mapping tool may then display the symbol at the location associated with the biopsy.

For example, the mapping tool may visual display a clinical findings associated with a liver superimposed on diagram of a liver. The clinical findings may include blood test results associated with the liver, a result of biopsy taken from the liver, a portion of the liver marked for future medical observation and/or a finding extracted from a radiograph or other medical image of the liver.

Symbols may be defined by color, shape, dotted lines, flashing indicators and more. Shapes and colors associated with a diagnosis may be customized by a user. Exemplary shapes and colors for different diagnoses are included in Table 1 below.

TABLE 1

| Symbol | Color | Diagnosis | Shape | Red | Green | Blue |
|---|---|---|---|---|---|---|
| ● | RED | Cancer | Solid Circle | 255 | 0 | 0 |
| ∆ | FUCHSIA | Precancer | Hollow Triangle | 255 | 0 | 255 |
| ⴷ | TEAL | Suspicious | Inverted Y | 0 | 128 | 128 |
| ☐ | BROWN | Benign | Hollow Square | 139 | 69 | 19 |
| x | PURPLE | Atypical | "x" symbol | 128 | 0 | 128 |
| Y | GREEN | Infectious | "Y" symbol | 0 | 128 | 0 |
| ◇ | BLUE | Inflammatory | Hollow Diamond | 0 | 0 | 255 |
| − | BLACK | Negative | Dash | 0 | 0 | 0 |
| ⬠ | AQUA | Other | Irregular Pentagon | 0 | 255 | 255 |
| + | ORANGE | Positive | Plus sign | 255 | 140 | 0 |
| ~ | BRIGHT GREEN | Pin (prostatic intraepithelial neoplasia) | Similarity symbol | 192 | 192 | 192 |
| ⌒ | GRAY | Non-Diagnostic | Arch | 210 | 180 | 140 |

A symbol "C," a circle with a question mark, or a flashing indicator may be used to represent a conflict between labs about a diagnosis of a biopsy. A flashing indicator may be used to represent a biopsy that has not yet been treated, or a biopsy for which results have not yet been received. A perimeter of a symbol may be turned into a dotted line if the margins of the biopsy site are not clear and more skin is required to be removed. A symbol "R" may be used to represent a biopsy diagnosed as rare and/or reportable.

In some embodiments, a color/shape of the symbol may represent the treatment of the biopsy (e.g. excised, laser or medicated). In some embodiments, a confluence of symbols may be used to indicate more than one test performed on a biopsy site, in addition to histology. For example, for each additional test, a line may be drawn through the symbol associated with the site. User selection or placement of a mouse over the biopsy site displayed on a body part image may initiate the display of a pop-up box including text detailing each of the tests performed at the biopsy location.

A symbol displayed on a body part image may be associated with some or all of the historical information entered for the biopsy into the biopsy marker record. In some embodiments, selection of the symbol may initiate a display of at least a portion of the biopsy's historical information. In some embodiments, selection of the symbol may initiate a display of a photograph taken of the biopsy location.

The mapping tool store information relating to one, two, three, or more biopsies taken from a patient. Each biopsy may be associated with a patient identifier and/or an accession number. The mapping tool may create for the biopsies one or more biopsy marker records, including historical information, as detailed above.

The mapping tool may store in one or more database(s) biopsy information for a plurality of patients. Biopsy marker records may be created for each of the plurality of patients and stored in the database(s). Historical data stored in the biopsy marker records includes the exemplary historical data described above and any other suitable data.

The mapping tool may be used to generate a report for a patient or, as detailed below, to display reports run by a user by selecting one or more search terms of criteria. For example, when a biopsy diagnosis is finalized by a lab, or a search is finished running, the mapping tool may generate a report. The generated report may be in any suitable electronic form, such as PDF (portable document format), Word document or Excel or any other suitable format. The report may be stored, integrated and/or transmitted into the patient's EMR, a physician's EMR system, the patient himself/herself, printed in hard copy, or transmitted in any other suitable fashion.

If the report is to be faxed in black and white, the report may use symbols to distinguish diagnostic categories or other criteria. Exemplary symbols include cancer—solid circle, precancer—hollow triangle, suspicious—plus sign and benign—hollow square.

In the embodiments where the report is generated for a single patient, the report may display some or all of the biopsies taken from the patient. The biopsies may be biopsies taken on a single date or over time. In the event that the report includes information relating to two or more biopsies taken from a single body part, the report may include a display of a body part image representing the body part and symbols representing each of the biopsies overlaid on the body part image. If the two or more biopsies were taken from different areas of the body, the report may include a display of each body part from which a biopsy was taken or an image of the entire human body with biopsy information displayed thereon.

Reports generated by the mapping tool may include one or more data fields and functionalities. For example, reports generated by the mapping tool may include a chart. The chart may include information detailing characteristics of biopsies displayed in the report. Exemplary information includes a date on which a biopsy was taken, an accession number associated with the biopsy, a location on the body where the biopsy was taken, the symbol associated with the biopsy, a category associated with the diagnosis, and the diagnoses. The chart may be customized by a user to display any suitable historical data. In some embodiments, the chart may be customized by a user to display user selected information.

In some reports generated by the mapping tool, selection of a symbol displayed on the body part image may highlight a row in the chart that includes information (e.g. a diagnosis) associated with the biopsy taken at the location where the symbol is displayed.

In some reports generated by the mapping tool, selection of a symbol displayed on the body part image may initiate a pop-up box displaying an actual photo taken of the biopsied area.

A user may access the mapping tool to run one or more searches. For example, the mapping tool may be accessed online by the user. After a secure log in, the user may search the database(s) using one or more search terms.

The mapping tool may search the database(s) to retrieve some or all biopsy data for a patient for any suitable time period or data on multiple patients filtered by category, diagnosis, site and any other criteria tied to the biopsy site. The mapping tool may search by accession number, patient identifier, or using one or more terms and/or criteria.

Exemplary search terms that may be used by the mapping tool to search the database(s) include searching the history of a single patient, a plurality of patients, or all patients based on one or more criteria. Exemplary criteria include data range (e.g. show all dates or select a date range), male/female, diagnosis (show all biopsies or choose by diagnosis—customizable: Cancer only, Cancer and Precancer, Infectious only), category of diagnosis (e.g. cancer can be broken down by type, into melanoma, Basal Cell Carcinoma, Squamous Cell Carcinoma), test type (e.g. Histology, FISH (skin, breast, prostate, esophagus) or Molecular Genetics), body part, body location (Example: Right, Left and other locations), site, laboratory, insurance of patient, whether or not a treatment has been paid for, physician, practice, and geographical area of patient(s) (e.g. county, town, state, country). Search terms may be customized by the user.

The mapping tool may run the search created by the user. The mapping tool may use the results of the search to generate one or more reports. The reports may illustrate various types of information. The reports may include diagnostic information overlaid on one or more body part images.

The tool may allow a user to customize the generated reports for different types of end users. Illustrative end users may include a patient, a physician, laboratory and/or insurance company. For example, a user may select a body part image to be used on a report for displaying biopsy information. A user may also select image size, information to be included on data charts, and other features that can be customized on reports. A user may also select an option for a report to include, on a first page, an image in small font embedded in text, and the same image displayed again, in large font, on a following page.

The diagrams generated by the mapping tool may be used for quick reference, downloaded and saved in a patient's EMR, or used in a presentation or study.

A report or body part image generated by the mapping tool may include any of the functionalities described in the application.

A report or image generated by the mapping tool may include a note adding feature. The note adding feature may enable a user to add one or more text boxes to the report/image. The user may add a text box by selecting the note tool, clicking on an area of interest, and typing text. The text box may point to the selected area of interest. The text box may visually identify to a user a location on the body that needs to be watched more closely. A user may add an "eye" symbol, or other indicator, to his note or to the image itself, alerting medical personnel to 'keep an eye on this.'

A selectable option in the mapping tool may include instructing the mapping tool to display all notes associated with a report or image, or to display all notes created during a predetermined time span.

A report or image generated by the mapping tool may include a "zoom-in" function and a "zoom-out" function. The zoom-in and zoom-out function may be used at any location on a displayed report/body part image.

The zoom-in function may enable a user to further distinguish overlapping biopsies (or other illustrative clinical findings), biopsy locations, or biopsy locations that are close together. In some embodiments, the zoom-in function may be automatically activated if a user places his mouse over a location of overlapping biopsies.

A report or image generated by the mapping tool may display a body part image or any other image or photograph in 2D or 3D.

A 3D image displayed by the mapping tool may include visual indicators of biopsies, or other clinical findings, taken at different locations around the 3D image. A 3D image displayed by the mapping tool may be an image of the entire human body, a portion of the human body, or one or more internal organs of the human body such as the colon, gastrointestinal ("GI") tract—upper/lower, prostate and other internal organs. In some embodiments, the mapping tool may use one or more of 3D image guided surgery and computerized axial tomography ("CAT") scans to create the 3D image(s).

In the embodiments where the body part image or any other image or photo is displayed in 3D, the mapping tool may include one or more interactive functionalities. For example, a user may rotate, pan, tilt and/or flip the image by clicking and dragging a mouse, using a touch screen monitor, or any other suitable methods.

A report or image generated by the mapping tool may display a body part image or other image or photograph in a transparent form. The transparent form may enable a user to view both a front and back portion of the body part image simultaneously. This transparency may assist a user in identifying where biopsies have been taken in organs such as the colon which has a tubular structure. Biopsies may displayed on the front wall, back wall, top or bottom of the transparent image.

The mapping tool may include one or more functionalities allowing a user to sort data and/or display data on two or more body part images. The data may be data retrieved using one or more search criteria described above.

For example, two or more body part images (referred to alternately hereinafter as "layers") may be generated to display subsets of data included in a data set of medical information. This may provide a viewer with in a visually display/sorting of search results in an easy to understand format. Exemplary criteria may include time period (e.g. current year, 1 year, 2 years, 5 years, all years), treatments (display which biopsies were treated), laboratories, sites, payments and other data. For example, a user may want to view all biopsies performed on a patient. A user may then select three different time periods. The mapping tool may then display three body part images, each body part image displaying biopsy data for the patient that was taken during one of the three different time periods.

Layers may be added or removed by a user by checking and unchecking criteria. Unchecking criteria may result in overlaying two or more layers and merging together the coordinates of symbols displayed on the displayed overlaid layers.

The mapping tool may include one or more functionalities for displaying biopsies, or other clinical data, on a body part image which are close in proximity to one another, or directly on top of each other.

In some embodiments, the mapping tool may display an arrow pointing to overlapping biopsies. In some embodiments, the overlapping biopsies may be identified by a flashing circle. In some embodiments, the overlapping area may be darker relative to other areas on the body part image. In some embodiments, the mapping tool may display a symbol on the overlapping site. In some embodiments, overlapping symbols may be displayed. In some embodiments, a flashing box may highlight the overlapping biopsy site. In some embodiments, the symbols for each overlapping diagnosis may flash alternately on the overlapping site. The displayed symbol may represent the most severe diagnosis associated with the biopsies located at the overlapping site.

The mapping tool may generate a visual display of medical information based on a hierarchy of pathological diseases. The hierarchy may rank pathological diseases by severity of diagnosis, urgency of treatment, or any other suitable criteria. In the event that the mapping tool identifies two or more overlapping biopsies, the mapping tool may use the hierarchy to identify an optimized pathological disease. The mapping tool may identify the optimized pathological disease by identifying, from a group of pathological disease associated with the overlapping biopsies, a pathological disease that is associated with the highest or lowest ranking value on the hierarchy relative to the other pathological diseases in the group.

The mapping tool may display, next to the overlapping site or on top of the overlapping site, a numerical value equal to the number of biopsies located at the overlapping site.

Placement of a cursor, or user selection of the overlapping site, may illuminate or generate diagnosis and diagnostic information on a chart associated with each of the biopsies located at the overlapping site.

For example, the mapping tool may include one or more functionalities for displaying a single biopsy with one or more diagnoses. In some embodiments, a symbol representing the more serious biopsy diagnosis may display at the site. Other functionalities may include the functionalities used by the mapping tool for displaying biopsies on a body part image which are close in proximity to one another, or directly on top of each other.

The mapping tool may include a recurrence alert. The recurrence alert may alert a user of the mapping tool of areas of a patient's body which have a greater chance of developing cancer or other diseases.

The mapping tool may implement the recurrence alert by comparing a lesion size/volume and/or a distance between a lesion and other lesions nearby with pre-established measurements. The measurements may be based upon scientific findings and integrated with published data proven to indicate, or correlated with, a recurrence. The mapping tool may run this alert for each biopsy displayed on a body part image. If one, two or more biopsies are found to be at risk for recurrence, the mapping tool may highlight the biopsies and/or areas around the biopsies that are at risk for recurrence.

For example, an image of a face may include a biopsy removed from the face. The recurrence alert may assess the length (1D), length and width (2D), or length, width and depth (3D) of the biopsy, and any other biopsies displayed on the face. Based on the 1D, 2D or 3D measurements of the biopsy and the other biopsies, the recurrence alert may search for previous biopsies within a 5 mm radius of the current biopsy.

The mapping tool may include "hot spot mapping." Hot spot mapping may be used to display the results of searches identifying clinical findings taken from multiple locations on a body part image. Hot spot mapping may be used to display the results of searches identifying clinical findings associated with a population. Hot spot mapping may be a user selectable option. In some embodiments, a search may default to hot spot mapping if more than a threshold number of clinical findings are associated with a body part image displayed by the mapping tool.

A user may run a hot spot search using the mapping tool by selecting one or more criteria to be applied to any suitable data set accessible via the tool. For example, a user may search the data set by type of cancer and patient demographics such as age, race and/or risk factors such as smoking and/or genetic predisposition.

The mapping tool may then identify a body part image associated with the search. The mapping tool may section the body part image into quadrants. In some embodiments, the quadrant sectioning may be correlated with the ICD-9 body part descriptions or any other suitable description or specification. ICD-9 is the International Classification of Diseases, Ninth Revision, Clinical Modification system used by health care providers to classify and code diagnoses, symptoms and procedures recorded in conjunction with hospital care in the United States.

The mapping tool may loop through all the biopsy marker records identified in the search and tally how many biopsies were found in each of the quadrants. If a biopsy has a boundary between two quadrants, the biopsy may be assigned to the quadrant in which a majority of the biopsy area is located. If the biopsy is located exactly in the middle of two quadrants, the mapping tool may alternate assigning of the biopsy to one of the two quadrants.

The generated image may color each quadrant based on a number of biopsies found in each quadrant. Two or more colors may be used for the shading. Each color may identify a numerical range of biopsies that are located in a quadrant shaded by that color. For example, a shading of deep red, light red and pink may be used, with each color representing a predetermined range of biopsies.

For laboratories that do not use diagrams, a text-to-plot system may be used by naming quadrants with site names that the laboratory uses such as upper left cheek, lower right chin and others. The biopsies may then be confined to that quadrant and the color range system may be applied (e.g. deep red—light pink/high quantity—low quantity, respectively) or the number of biopsies can display within the quadrants.

At set forth above, the mapping tool may be used to run a plurality of searches and generate a wide range of images and reports. Additional exemplary searches and reports executed by the mapping tool are detailed below.

In some embodiments, the mapping tool may be used to search for instances of discordance between two or more labs (i.e. when a second consultation from a lab resulted in a different diagnosis). This search may be modified by one or more criteria identified above. For example, selection of a "show conflicts" option may present a user with search options such as viewing conflicts by site, by laboratory, by diagnosis, by body part, and any other suitable criteria. If multiple labs are selected and displayed on a single diagram, medical test results generated by different laboratories may each be differentiated by color and/or symbol.

In some embodiments, the mapping tool may be used to track improper specimen handling by site. Examples of improper specimen handling include site mismatch, name mismatch, submitted in expired media, submitted in incorrect media (e.g. formalin versus ThinPrep), and inadequate specimen (e.g. not enough sample from patient or not enough removed). These problems can be differentiated by color/symbol or mixture of both. The mapping tool may allow a user to filter problem data by site, by physician, practice, lab and any other suitable data. Selection of a biopsy, or other indicator displayed on body part image, may initiate a display of a text box including more information such as site of specimen taken and problems with specimen.

In some embodiments, the mapping tool may be used by a group practice to optimize treatment plans. For example, a search may be run by searching all clinical data associated with a group practice and generating a diagram displaying all of the group's biopsies, treatments and results. This report may enable the group practice to streamline methods and treatments based on effectiveness.

In some embodiments, the mapping tool may use historical data to determine the effectiveness of one type of treatment in comparison to a second type of treatment. For example, symbols, colors and highlighting options, may be selected by a user of the mapping tool to display data for patients with cancer treated with "A" procedure/treatment/technique and to display and compare results to patients treated with "B" procedure/treatment/technique. A special symbol may appear on the diagram where each biopsy was taken, and the symbol may be highlighted if that site had a lower complication rate and/or higher cure rate of cancer. This may assist the practice in visualizing whether a complication/cure is more frequent on certain parts of the body depending upon which treatment modality was used or if a lack of effectiveness by treatment is responsible for a complication or cure.

For example, Mohs Micrographic Surgery (MMS) is a highly specialized treatment method used to remove two of the most common skin cancers, Basal Cell Carcinoma (BCC) and Squamous Cell Carcinoma (SCC) while salvaging as much healthy tissue as possible and leaving minimal scarring on sensitive areas such as the face. This treatment has the highest cure rate and is performed in one day allowing for patients to recover quickly. A new study released by the American Academy of Dermatology in 2012 evaluated the use of Mohs surgery and updated its criteria on which lesions it should be used for based on factors such as area of body, lesion size, patient characteristics and tumor characteristics. An article published by the New York Times in January 2014 investigated the overuse of Mohs surgery and found that physicians performed this method of removal over 400 percent more than a decade ago prompting Medicare to add it to the top of their list of "potentially misvalued" overused or overpriced procedures.

The mapping tools may be used to display areas on the body in which Mohs is appropriately or inappropriately used. The selectable criteria can be superimposed on a desired body location/image to differentiate proper or improper use on the selected body location. For example, in some embodiments, the mapping tool may include one symbol for excision and a different symbol for a Mohs procedure. If the symbol is hollow, the treatment cured the patient. If the symbol is filled in, the treatment had complications. Thus, the mapping tool can be used to illustrate whether or not Mohs has more cures and less complications in comparison to excisions.

In some embodiments, the mapping tool may be used to identify which biopsies, or other clinical procedures, have been paid for, have not been paid for yet by an insurance company, or which biopsies have not been paid for yet by all insurance companies. The tool may identify a trend by insurance companies and put procedures in place to follow up with those insurance providers that lag in payment by diagnosis or other criteria.

In some embodiments, the mapping tool may be used to identify trends in which certain biopsies or other clinical procedures, take the longest to be reimbursed. For example, a user of the mapping tool may identify, using one or more diagrams output by the mapping tool, that prostate biopsies take longer to be reimbursed because there of discrepancies relating to the amount of biopsies that need to be taken, or because of missing information.

In some embodiments, the mapping tool may be used to create one or more reports that assist a user in identifying unnecessary test(s) ordering by site or costly techniques used by a physician when a less invasive, less expensive method of removal or treatment could have been performed. For example, a user may run a report in the mapping tool that displays which physicians used invasive techniques for non-invasive conditions or discordance of treatment versus technique according to published data. These results may be viewed overlaid on a body part image by biopsy location, patient insurance, treating physician or any other suitable criteria.

In some embodiments, the mapping tool may be used to create one or more reports to assist a user in identifying which physicians or practices take more biopsies based on patient insurance. For example, a user may use the mapping tool to run a report by searching the criteria "biopsies" and "insurance plan," and customize the biopsy displays to be represented by color/symbol associated with an insurance plan/provider. The report may be viewed on one diagram. The report may include many layers, each layer being associated with an insurance plan and, in some embodiments, a body image.

In some embodiments, the mapping tool may be used to create one or more reports to visually display, for a particular body part, which labs diagnose cancer more frequently than other labs by location, by searching by diagnosis and laboratory. The search results may be overlaid on a body part image. This information may be useful for insurance companies at least because over-diagnosing by a laboratory desiring to ingratiate themselves with a physician or practice can signal fraud or abuse as the doctor will receive more money based on a diagnosis of cancer (Preventing over diagnosis: how to stop harming the healthy. BMJ2012; 344:e3502.)

The mapping tool may also be used to display a number of biopsies or other clinical procedures, performed by a medical practice based on a patient's insurance status (insurance provider, self-pay, uninsured or indigent patients). In some embodiments, each biopsy taken may be displayed by a symbol associated with the insurance of the patient. A report generated may include a single image with all biopsy data or a separate image for each insurance status. Trends in increase of biopsies or testing by type of patient insurance, or lack thereof, can signal possible abuse by physicians because insurance carriers pay differently for certain procedures and tests performed.

In some embodiments, the mapping tool may be used by healthcare researchers to identify any increase in cancer incidence, or changes in cancer incidence, on a particular site by gender, race, age, geographical area. Society would then possible be able to counteract this cancer trend through education and other appropriate measures. The mapping tool may also be used by healthcare researches to identify hot spots. Furthermore, the mapping tool may enable a user to identify and view recurrence rates or cure rates by site, by method of treatment, by age and/or gender or any suitable demographic criteria.

Benefits include quickly identifying trends in cancer, precancer and other diseases, biopsy adequacy, concordance rates and the most effective treatments for patients while reducing healthcare costs at the same time. The mapping tools may be implemented to standardize lab reporting methods nationally and achieve complete integration of information among a plurality of laboratories, or all laboratories. This technology can be adopted into any healthcare establishment and customized to their specifications.

One of ordinary skill in the art will appreciate that the steps shown and described herein may be performed in other than the recited order and that one or more steps illustrated may be optional. The methods of the above-referenced embodiments may involve the use of any combination of methods, portions of methods, partially executed methods, elements, one or more steps, computer-executable instructions, or computer-readable data structures disclosed herein. Embodiments may include printing, on paper, visualization of diagnoses on a body part image.

As will be appreciated by one of skill in the art, the invention described herein may be embodied in whole or in part as a method, a data processing system, or a computer program product. Embodiments disclosed herein may be partially or wholly implemented on a computer-readable medium, for example, by storing computer-executable instructions or modules or by utilizing computer-readable data structures. Accordingly, the invention may take the form of an entirely hardware embodiment, an entirely software embodiment or an embodiment combining software, hardware and any other suitable approach or apparatus.

Furthermore, such aspects may take the form of a computer program product stored by one or more computer-readable storage media having computer-readable program code, or instructions, embodied in or on the storage media. Any suitable computer readable storage media may be utilized, including hard disks, CD-ROMs, optical storage devices, magnetic storage devices, and/or any combination thereof. In addition, various signals representing data or events as described herein may be transferred between a source and a destination in the form of electromagnetic waves traveling through signal-conducting media such as metal wires, optical fibers, and/or wireless transmission media (e.g., air and/or space).

Illustrative embodiments of apparatus and methods in accordance with the principles of the invention will now be described with reference to the accompanying drawings, which form a part hereof. It is to be understood that other embodiments may be utilized and structural, functional and procedural modifications may be made without departing from the scope and spirit of the present invention.

FIG. 1 shows an illustrative portion of report 100 generated by the mapping tool. Report 100 includes body part image 103. Body part image 103 includes three symbols from three different dates of service overlaid on top of body part image 103. It would be difficult to realize the special relationship amount the diagnoses represented by the three symbols without the superimposition of the diagnoses on body part image 103. Legend 105 details a diagnosis associated with each of the three symbols.

A mouse is displayed overlaid on report 100. Placement of the mouse over of the cancer symbol displayed on body part image 103 is shown to generate gross image 107. Gross image 107 is a photograph taken of the cancer site prior to a biopsy. Placement of the mouse over the displayed body part image 103 is also shown to generate chart 109. Chart 109 includes the following columns: date 111, accession number 113, site 115, symbol 117, category 119, diagnosis 1221 and customized columns 123. The columns in chart 109 are populated with data associated with each of the symbols overlaid on body part image 103.

It should be noted that, in other embodiments, when a mouse is placed over one of the symbols overlaid on body part image 103, chart 109 may highlight a column in the chart that includes information describing the "placed over" symbol. In yet other embodiments, when a mouse is placed over one of the symbols overlaid on body part image 103, a chart may be displayed that includes information only relating to the "placed over" symbol.

Figure 2:
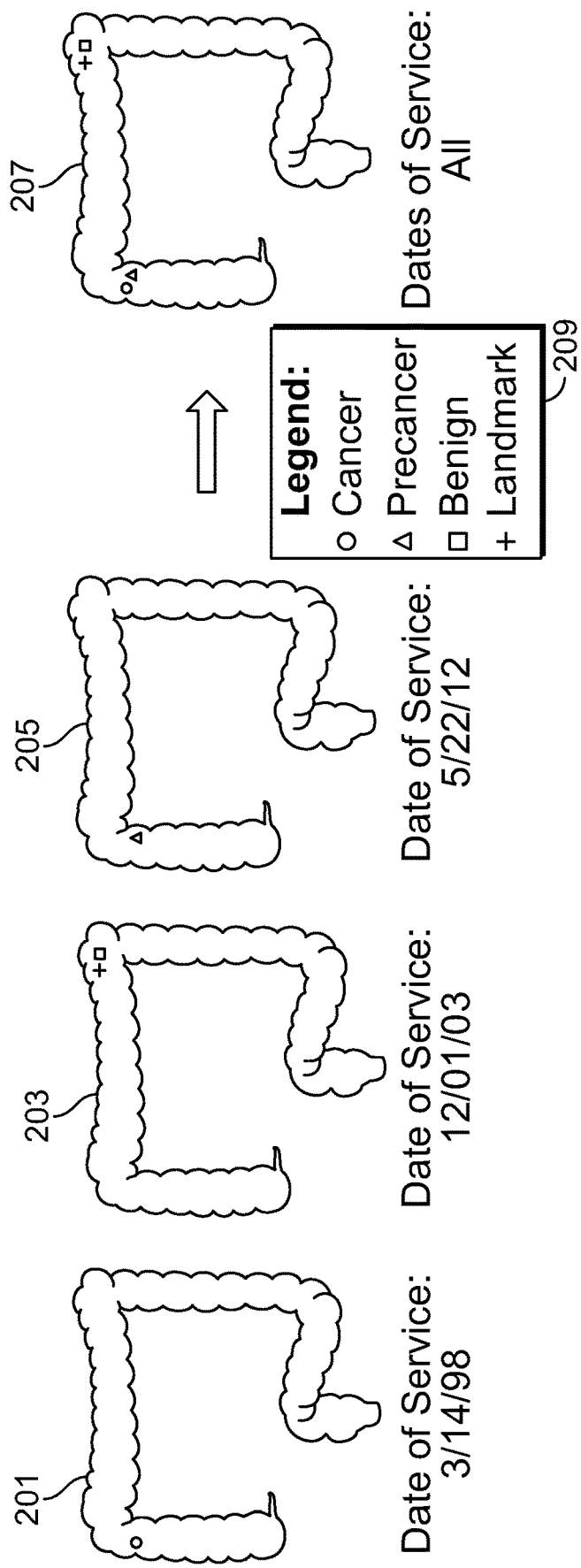
FIG. 2 shows another illustrative graphical user interface for use with the systems and methods of the invention.

FIG. 2 shows an illustrative portion of one or more reports that may be generated by the mapping tool. The report shown in FIG. 2 illustrates a body part image representing a colon of a patient. The patient has had three biopsies taken from the colon on Mar. 14, 1998, Dec. 1, 2003, and May 22, 2014. Each biopsy has been diagnosed.

Body part images 201, 203 and 205 illustrate images generated by the mapping tool. The images may be generated by the mapping tool in response to a user selection to view the biopsies separately by selecting date of service or any other suitable user selection. Each of body part images 201, 203 and 205 show information relating to a biopsy. The biopsy information illustrated in each of body part images 201, 203 and 205 is conveyed to the user at least by (1) displaying a symbol associated with the diagnosis of the biopsy and (2) displaying the symbol in the location where the biopsy was taken. Legend 209 includes text informing a user of the diagnosis associated with each of the symbols.

Body part image 207 illustrates an image generated by the mapping tool in response to a user selection to view all biopsies on a single body part image or any other suitable selection. Body part image 207 illustrates all three biopsies taken for the patient layered on a single image.

Figure 3:
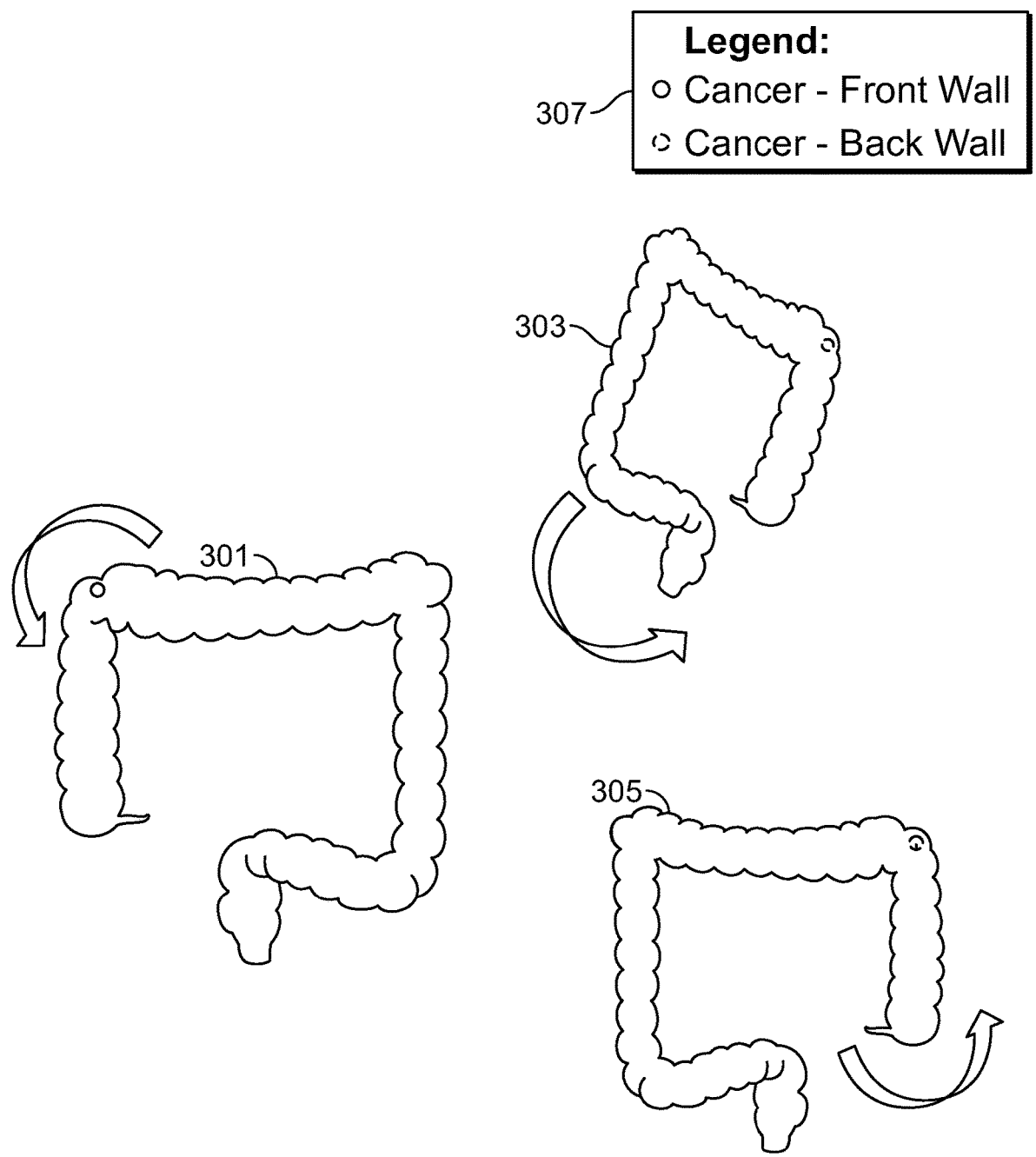
FIG. 3 shows yet another illustrative graphical user interface for use with the systems and methods of the invention.

FIG. 3 shows illustrative functionalities of the mapping tool. Body part image 301 represents a front view of a colon of a patient. Body part image 301 includes a symbol identifying a cancerous lesion found on the front wall of the colon. Symbols representative of diagnosis or other clinical finding may change over time. For example, a lesion may initially be classified by a clinician as precancer. Later in time, the lesion may be reclassified as cancer. A body part image may include symbols that show the evolution of clinical findings associated with the lesion. For example, the different diagnoses associated with a lesion may each form a layer that may be overlaid on a single body part image. The clinician or other user may select which layers (for example based on date) may be overlaid on the body part image.

Such tools for overlaying diagnoses associated with a body location also allow clinician to easily differentiate between new clinical findings and recurrences of prior clinical findings. For example, if a new clinical finding is made in a location that was previously associated with different finding, the new finding may be classified as a recurrence.

Body part images 303 and 305 show views of the colon that are different from the view of the colon shown by body part image 301. Body part image 303 and 305 represent a back view of the colon. Body part images 303 and 305 include a symbol identifying a cancerous lesion found on the back wall of the colon.

A user may generate body part images 303 and 305 by selecting body part image 301. The user may select body part image 301 by clicking a mouse, using a touch screen monitor, or by any other suitable methods. The user may then rotate, pan, tilt and/or flip body part image 301 to create body part images 303 and 305.

Body part images 303 and 305 are illustrative views of a colon that may be generated by a user. Any other suitable image of a colon may be generated by a user by rotating, panning, tilting and/or flipping body part image 301.

In some embodiments, the mapping tool may display different views of the colon, in addition to information identifying biopsies and/or diagnoses associated with the different views of the colon, independent of user selections. In some embodiments, the mapping tool may superimpose diagnoses on associated with a colonoscopy, endoscope or other suitable video material (such as video captured by an ingested "video pill").

FIGS. 4A-4B shows an illustrative dermatopathology report generated by the mapping tool. The illustrative report includes information 401. Information 401 details a patient's information, specimen information, and surgery/physician information.

The illustrative report also includes diagnosis information. Diagnosis information is displayed in text box 403, text box 405 and text box 407. Text box 403 includes text detailing the diagnosis of lesion A found on the patient. Text box 405 includes text detailing the diagnosis of lesion B found on the patient. Text box 407 includes text detailing the diagnosis of lesion C found on the patient.

The illustrative report also includes body part image 409. Body part image 409 illustrates the location, on the body, where lesions A, B and C were found. This information is displayed by overlaying the letters A, B and C on the area of the body part image where the lesions were found. Letters A, B and C may represent lesions examined on different dates. Letters A, B and C may represent lesions examined on different dates by different laboratories. In other embodiments, a symbol representing a diagnosis of each lesion may be overlaid on the location where the lesions were found.

The illustrative report also includes photomicrograph 411, photomicrograph 413 and photomicrograph 415. Photomicrograph 411 displays a photograph of lesion A. Photomicrograph 413 displays a photograph of lesion B. Photomicrograph 415 displays a photograph of lesion C.

The illustrative report further includes color keys 417. Color keys 417 displays a plurality of symbols that may be included on an illustrative report generated by the mapping tool. Color keys 417 include text detailing a diagnosis associated with each of the color keys.

Figure 5:
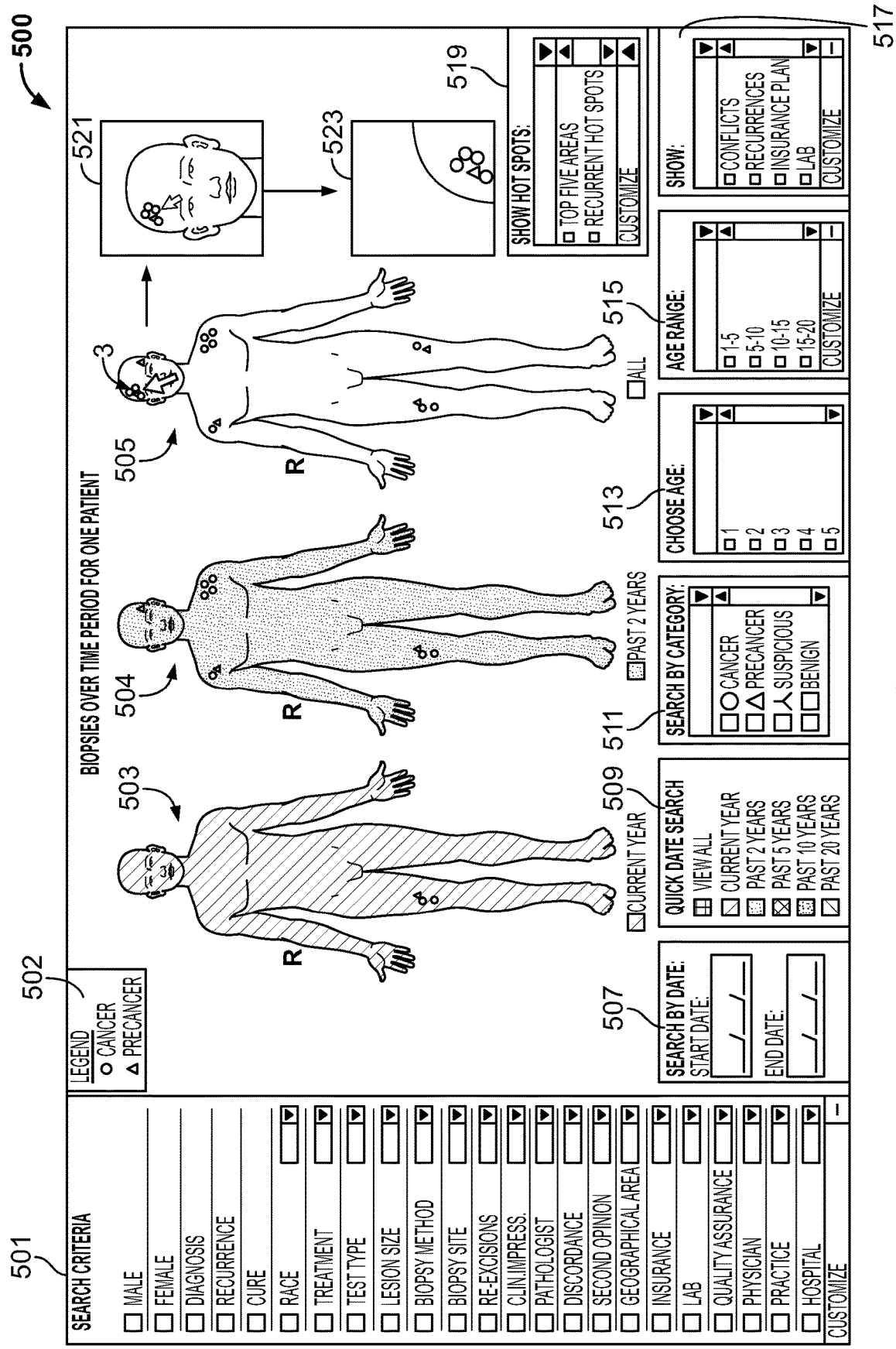
FIG. 5 shows yet another illustrative graphical user interface for use with the systems and methods of the invention.

FIG. 5 shows an illustrative GUI 500 that may be generated by the mapping tool. GUI 500 includes body part image 503, body part image 504 and body part image 505. Body part image 503 includes biopsy information for a patient during the current year. Body part image 504 includes biopsy information from the patient during the past two years. Body part image 505 includes all biopsy information for the patient.

Body part image 505 includes a plurality of overlapping symbols on the face portion of the body part image. The mapping tool has generated an arrow pointing to the overlapping symbols. The mapping tool has also displayed the number '3' next to the arrow. The number 3 is a number of symbols that are overlapping on the face portion of the body part image at the displayed zoom level of GUI 500.

GUI 500 includes legend 502. Legend 502 may display symbols that may be used by the mapping tool to illustrate a diagnosis of a biopsy. Legend 502 may also display a diagnosis associated with each symbol displayed on a body part image.

A user has placed a mouse next to a plurality of overlapping symbols displayed on body part image 505. Placement of the mouse next to the overlapping symbols may generate one or both of pop up box 521 and pop up box 523. Box up box 521 and pop up box 523 illustrate an enlarged view of a portion of the body part image. The portion of the body part image includes the symbols that were at least partially overlapping in image 505.

GUI 500 includes a plurality of options that may be selected by a user to generate one or more reports. Selection of the plurality of options may be used refine data displayed for the patient. Selection of the plurality of options may be used to generate new images including data for a different patient or for a plurality of patients. Selection of different options may instruct the mapping tool to generate an image based on different sources of medical information.

The plurality of options included on GUI 500 include search criteria 501, search by date 507, quick date search 509, search by category 511, choose age 513, age range 515, show 517 and show hot spots 519.

Figure 6:
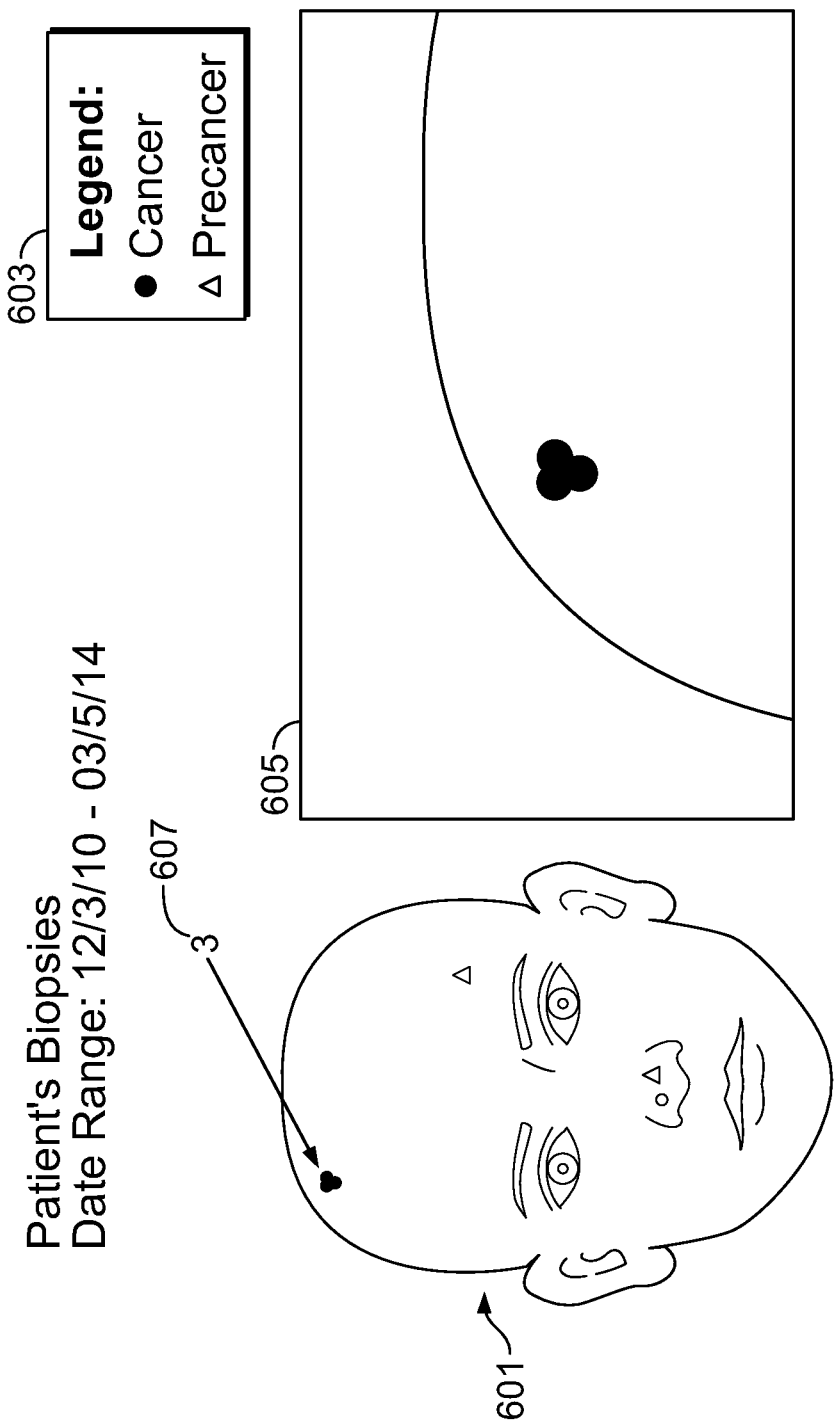
FIG. 6 shows yet another illustrative graphical user interface for use with the systems and methods of the invention.

FIG. 6 shows a portion of an illustrative report that may be generated by the mapping tool. The illustrative report includes a patient's biopsies taken between Dec. 3, 2011, and Mar. 4, 2014. The illustrative report includes body part image 601. Symbols identifying lesions and diagnosis of lesions found on the patient between Dec. 3, 2001, and Mar. 4, 2014, are overlaid on body part image 601. Legend 603 includes symbols that may be displayed by the mapping tool and a diagnosis associated with each of the symbols.

Three symbols are overlaid on body part image 601. A portion of each of the three symbols overlaps a portion of another one of the three symbols. In some cases, each of the three symbols may completely overlap each other. The illustrative report includes an arrow pointing to the overlapping symbols. The illustrative report also displays a number 3 next to the arrow. The number 3 represents the number of overlapping lesions found on the patient.

The illustrative report also includes zoom-in view 605. Zoom-in view 605 may be initially included in the report, or may be displayed upon user selection of the overlapping area, the number 3, or any other suitable selection. Zoom-in view 605 displays an enlarged image of the portion on body part image 601 where the overlapping symbols are displayed.

Figure 7:
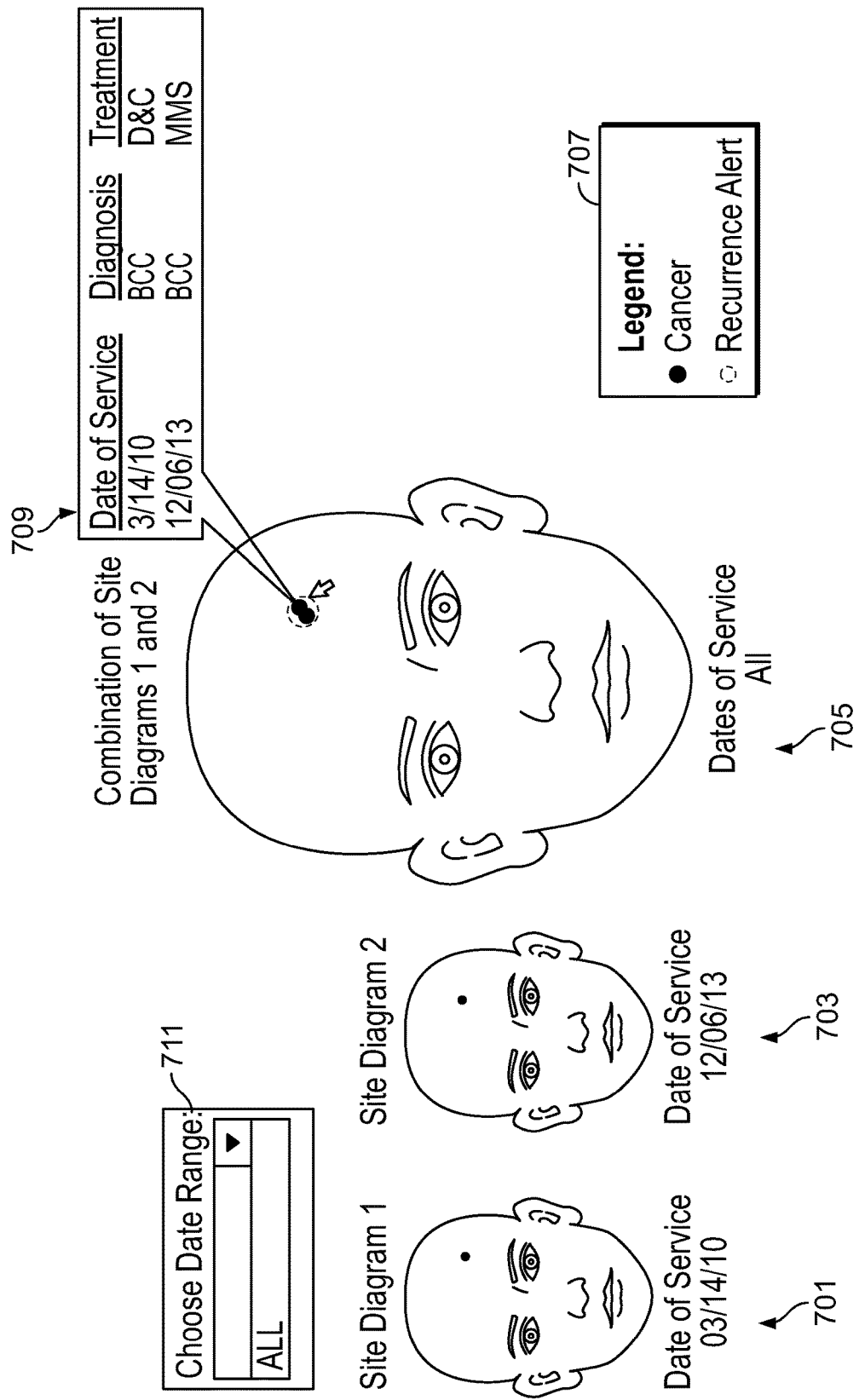
FIG. 7 shows yet another illustrative graphical user interface for use with the systems and methods of the invention.

FIG. 7 shows one or more portions of one or more illustrative reports that may be generated by the mapping tool. FIG. 7 includes body part image 701 and body part image 703. Body part image 701 includes a circular symbol. The circular symbol is associated with a cancer diagnosis (as shown in legend 707). The circular symbol is overlaid on body part image 701 at the location where a cancerous lesion was found on a patient on Mar. 3, 2010.

Body part image 703 also includes a circular symbol. The circular symbol is overlaid on body part image 703 at the location where a cancerous lesion was found on the patient on Dec. 6, 2013.

FIG. 7 also includes body part image 705. Body part image includes the symbol displayed on body part image 701 and the symbol displayed on body part image 703. In some embodiments, body part image 705 may be displayed by a user by choosing the option 'ALL' in the drop down box 711.

Body part image may include a recurrence alert symbol. The recurrence alert symbol is displayed on body part image 705 and surrounds the two overlapping cancer symbols. The mapping tool may generate the recurrence alert based at least in part on the proximity of the two cancer symbols to each other, a type of cancer diagnosis associated with each of the lesions, a two dimension width and/or a three dimensional depth of each of the lesions, medical research and any other suitable information. A recurrence alert may be generated based on clinical findings in the vicinity of previous diagnosis. In some embodiments, the proximity that may trigger a recurrence alert may be customized by a user of the mapping tool.

Recurrence alerts generated by the mapping tool may indicate to a physician that preventative steps should be taken. In the past, it has been difficult in clinical practice and as noted in publications to determine if a lesion is a new cancer or a recurrence. This sequential mapping recurrence alert can help solve this difficult problem by allowing for better analysis of the success or failure of a particular device or surgical technique.

A mouse has been placed in close proximity to the recurrence alert. In some embodiments, the placement of the mouse next to the recurrence alert has generated chart 709. In other embodiments, chart 709 has been generated together with body part image 705.

Chart 709 includes details for each of the two lesions. The details include a date of service, a diagnosis and a treatment.

FIG. 7 also includes legend 707. Legend 707 identifies a diagnosis or alert associated with symbols that may be displayed by the mapping tool on one or more reports.

Figure 8:
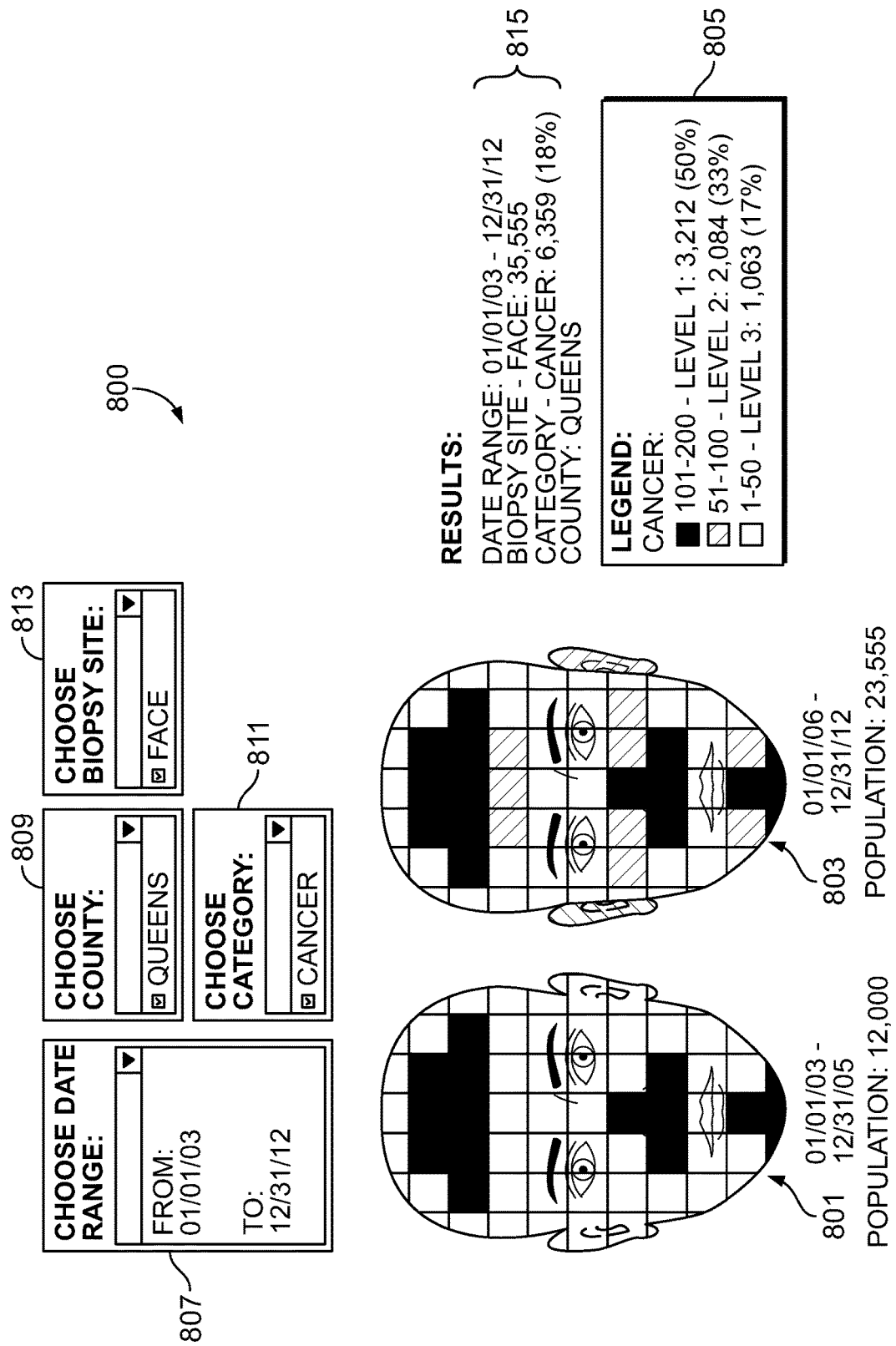
FIG. 8 shows yet another illustrative graphical user interface for use with the systems and methods of the invention.

FIG. 8 shows an illustrative visual report that may be generated by the mapping tool. The illustrative report includes an example of a report generated by the mapping tool using hot spot mapping. The hot spot mapping shown in the illustrative report was generated based on the following user-selected criteria: in choose date range box 807, a date range of Jan. 1, 2003-Dec. 31, 2012 was selected, in choose county 809, the county of queens was selected, in choose category box 811, cancer was selected, and in choose biopsy site 813, the face was selected.

The results of the user-defined search may be output, by the mapping tool, on one or both of body part image 801 and body part image 803. Each of body part image 801 and body part image 803 are sectioned into quadrants. As shown, body part image 801 includes data associated with the date range from Jan. 1, 2003-Dec. 31, 2005 based on medical information associated with a population that numbers 12,000. As shown, body part image 803 includes data associated with the date range from Jan. 1, 2006-Dec. 31, 2012 based on medical information associated with a population that numbers 23,555.

The quadrants may be based on ICD-9 body part descriptions or other ICD specifications (such as nos. 10 or 11) criteria stored in the mapping tool. Some of the quadrants in body part images 801 and 803 are shaded.

Legend 805 correlates the shading, or lack of shading, of a quadrant to a number of cancer lesions found in the quadrant based on population data stored in a database accessible to the mapping tool. In some embodiments, body part image 308 may be generated in response to a selection of the black shading detailed on Legend 805.

Additional details of the results of the user-defined search are found on portion 815 of the report.

Figure 9:
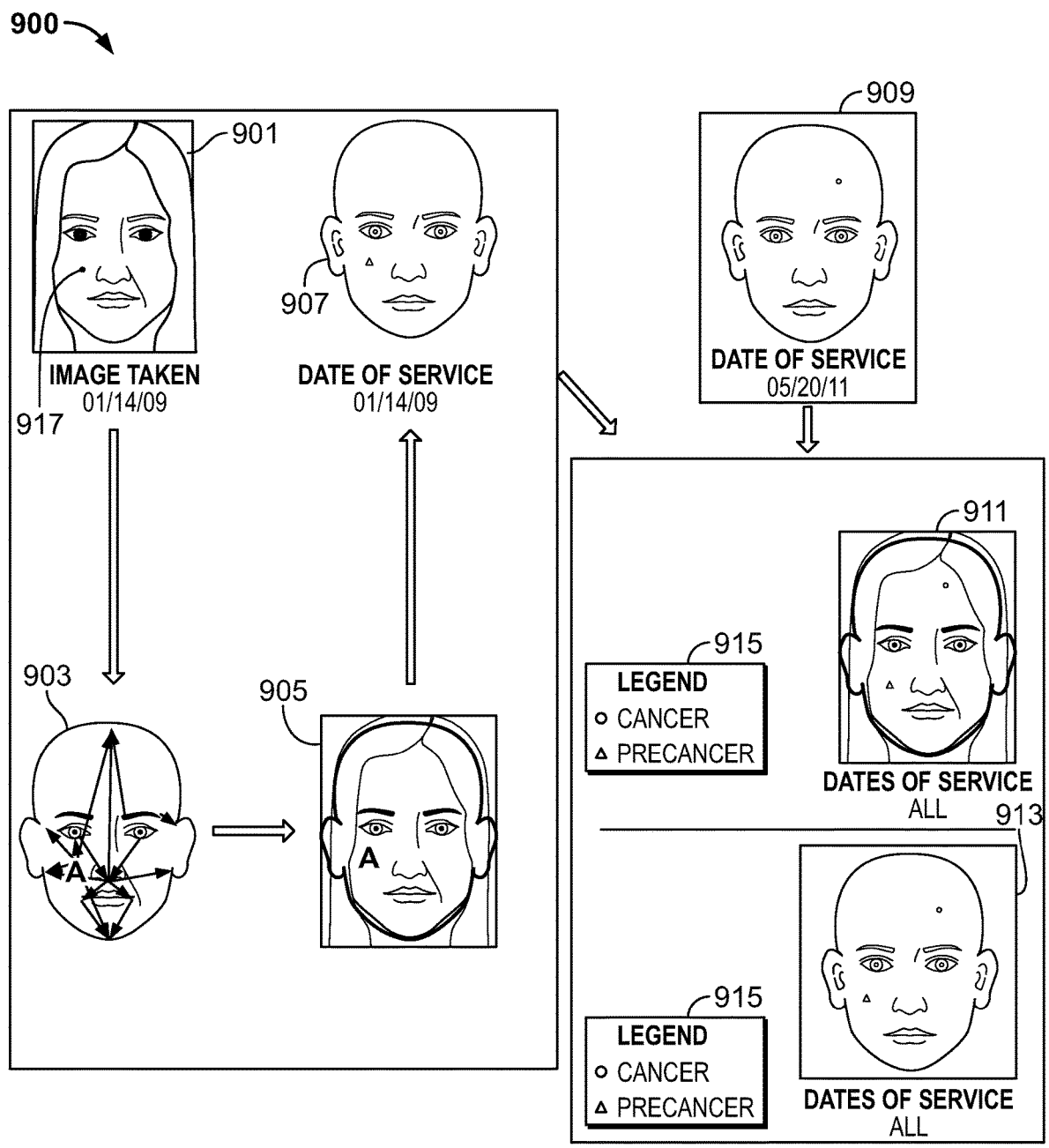
FIG. 9 shows yet another illustrative graphical user interface for use with the systems and methods of the invention.

FIG. 9 illustrates diagram and photo fusion routine 900 executed by the mapping tool. Photo fusion routines executed by the mapping tool, such a routine 900, may be utilized for a colonoscopy, endoscopy, or radiographic images. Routine 900 may include receiving photograph 901. Photograph 901 may represent a photograph of a patient taken on Jan. 14, 2009. The patient may have darkened skin area 917 on the upper right cheek.

Routine 900 may then include using image recognition software to identify match points on body part image 903. Routine 900 may subsequently include overlaying body part image 903 on top of photograph 901 by aligning the identified match points with corresponding features in photograph 901. Image 905 shows photograph 901 with body part image 903 overlaid on top of photograph 901.

Once body part image 903 is overlaid on photograph 901, the location of darkened skin area 917 may be automatically plotted onto body part image 903. After the plotting, routine 900 may include generating body part image 907. Body part image 907 may include a symbol representing darkened skin area 917.

Routine 900 may further include integrating body part image 909 with body part image 907 and/or photograph 901. Body part image 909 may include a symbol overlaid on body part image 909. The symbol represents a lesion found on the patient on May 20, 2011.

The integration of body part image 909 with photograph 901 may generate hybrid photograph-image 911. Hybrid photograph-image 911 may include photograph 901, without the darkened skin region. Overlaid on top of photograph 901 may be an outline of body part image 909. Two symbols may also be overlaid on top of photograph 901. The triangular symbol may represent the lesion found on the patient on Jan. 14, 2009. The circular symbol may represent the lesion found on the patient on May 20, 2011.

The integration of body part image 909 with body part image 907 may generate body part image 913. Body part image 913 may include a triangular symbol and a circular symbol. The triangular symbol may represent the lesion found on the patient on Jan. 14, 2009. The circular symbol may represent the lesion found on the patient on May 20, 2011.

The mapping tool may display legend 915 next to each of hybrid photograph-image 911 and body part image 913. Legend 915 may include symbols used by the mapping tool and a diagnosis associated with each of the symbols.

Figure 10:
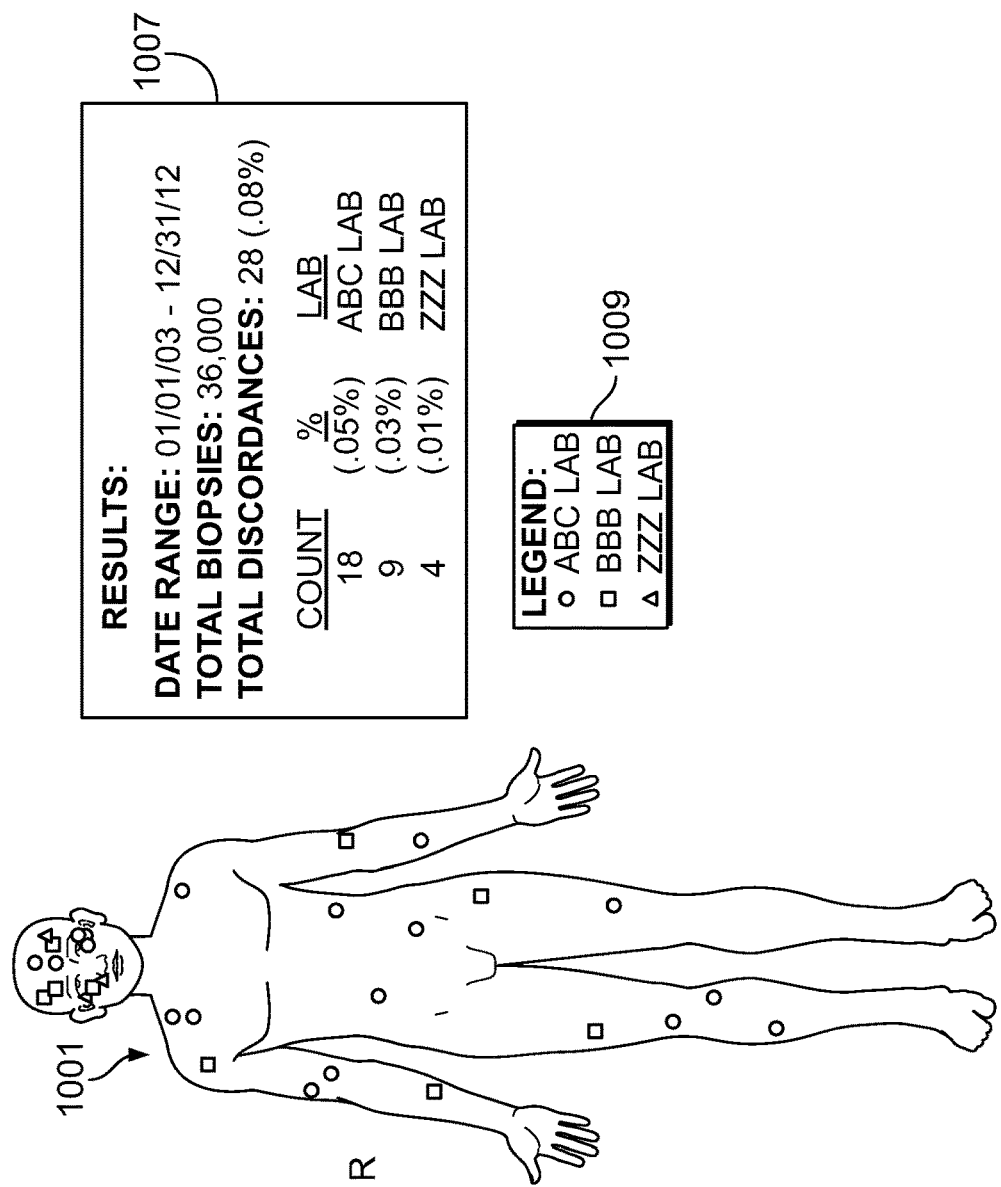
FIG. 10 shows yet another illustrative graphical user interface for use with the systems and methods of the invention.

FIG. 10 shows an illustrative report that may be generated by the mapping tool. The illustrative report may have been generated in response to the following user selections: in choose date range 1103, a selection of the date range Jan. 1, 2003 to Dec. 31, 2012, in choose labs 1005, a selection of ALL. An additional user-selection (not displayed) may include selecting 'view discordances.' Discordance may refer to a biopsy diagnosis, issued by a second lab, that differs from an opinion issued by a first lab.

In response to the user-defined selections, the mapping tool may generate a search and output the illustrative report. The illustrative report may include body image 1001. Symbols may be overlaid on body image 1001. Each symbol may represent medical information generated by one of labs ABC, BBB and ZZZ. Each symbol overlaid on body image 1001 may represent a discordance of opinion for the associated laboratory. The discordance of opinion may be related to a biopsy taken from an area of the body on which the symbol is overlaid. The discordance may be between a first lab and one of the labs ABC, BBB and ZZZ.

Body image 1001 may assist a user in visually identifying locations on the body where discordances between labs frequently occur.

The illustrative report may also include results 1007. Results 1007 may include details of the search terms and the discordances found for each of labs ABC, BBB and ZZZ.

In some embodiments, a user may execute a selection to view the discordances of each lab on a different body part image. In these embodiments, the mapping tool may generate three body part images. Each body part image may display symbols identifying locations of lesions on the body for which a discordance of opinion has occurred. When the discordances of the labs are viewed side by side, a user may easily identify which lab has a higher discordance rate.

Figure 11:
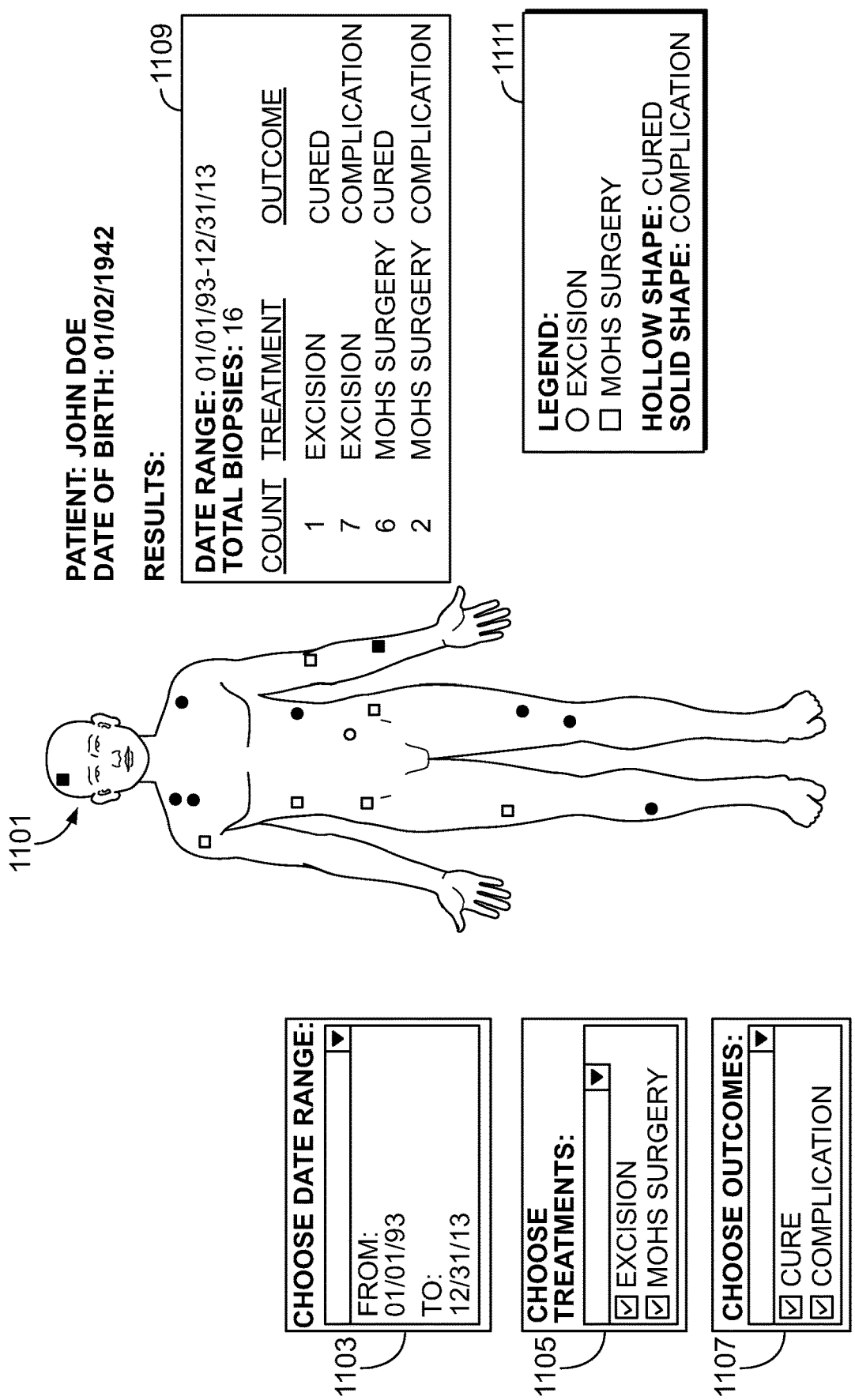
FIG. 11 shows yet another illustrative graphical user interface for use with the systems and methods of the invention.

FIG. 11 shows an illustrative report generated by the mapping tool. The report may be generated in response to a user selecting: from choose date range 1103, a date range of Jan. 1, 1993 to Dec. 31, 2013, from choose treatments 1105, the treatments of excision and Mohs surgery, and from choose outcomes 1107, the outcomes of cure and complication.

The illustrative report may include body part image 1101. Body part image may include symbols for each of the excision and Mohs surgery treatments performed by health practitioner between Jan. 1, 1993 and Dec. 31, 2013. The symbols displayed on body part image 1101 identify a location of each of the surgeries and whether or not the surgery cured the problem or resulted in complications.

The illustrative report may include legend 1111. Legend 1111 may identify symbols used by the mapping tool to illustrate surgeries and outcomes of the surgeries. The illustrative report may also include results 1109. Results 1109 may include parameters of the search and a summary of the search results.

The illustrative report generated by the mapping tool may assist a user in determining whether or not Mohs surgery has more cures and less complications in comparison to excisions. The illustrative report can also assist a user in identifying differences between Mohs and excisions based on body location.

Figure 12:
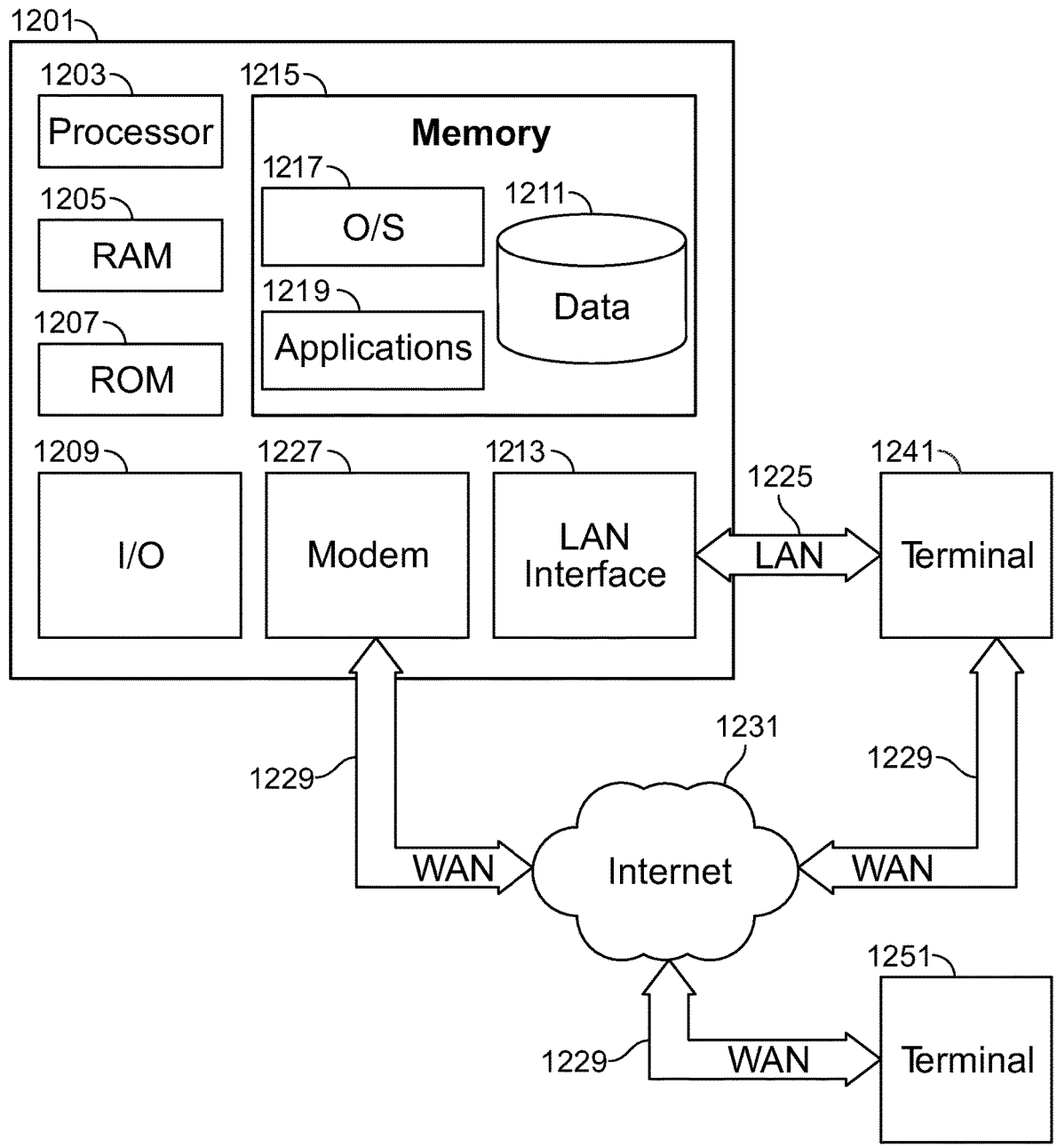
FIG. 12 shows illustrative computing apparatus for use with the systems and methods of the invention.

FIG. 12 shows a block diagram that illustrates a computing device 1201 (alternatively referred to herein as a "server or computer") that may be used according to an illustrative embodiment of the invention. The computer server 1201 may have a processor 103 for controlling overall operation of the server and its associated components, including RAM 1205, ROM 1207, input/output ("I/O") module 1209, and memory 1215.

I/O module 1209 may include a microphone, keypad, touch screen and/or stylus through which a user of device 1201 may provide input, and may also include one or more of a speaker for providing audio output and a video display device for providing textual, audiovisual and/or graphical output. Software may be stored within memory 1215 and/or other storage (not shown) to provide instructions to processor 1203 for enabling server 1201 to perform various functions. For example, memory 1215 may store software used by server 1201, such as an operating system 1217, application programs 1219, and an associated database 1211. Memory 1215 may store software used by server 1201 to render images, overlay medical information or perform any suitable function of the mapping tool. Database 1211 may include a plurality of distributed databases. Alternatively, some or all of computer executable instructions of server 1201 may be embodied in hardware or firmware (not shown).

Server 1201 may operate in a networked environment supporting connections to one or more remote computers, such as terminals 1241 and 1251. Terminals 1241 and 1251 may be personal computers or servers that include many or all of the elements described above relative to server 1201. The network connections depicted in FIG. 12 include a local area network (LAN) 1225 and a wide area network (WAN) 1229, but may also include other networks. When used in a LAN networking environment, computer 1201 is connected to LAN 1225 through a network interface or adapter 1213. When used in a WAN networking environment, server 1201 may include a modem 1227 or other means for establishing communications over WAN 1229, such as Internet 1231.

It will be appreciated that the network connections shown are illustrative and other means of establishing a communications link between the computers may be used. The existence of any of various well-known protocols such as TCP/IP, Ethernet, FTP, HTTP and the like is presumed, and the system can be operated in a client-server configuration to permit a user to retrieve web pages from a web-based server. Any of various conventional web browsers can be used to display and manipulate data on web pages.

Additionally, application program 1219, which may be used by server 1201, may include computer executable instructions for invoking user functionality related to communication, such as email, short message service (SMS), and voice input and speech recognition applications.

Computing device 1201 and/or terminals 1241 or 1251 may also be mobile terminals including various other components, such as a battery, speaker, and antennas (not shown). Terminal 1251 and/or terminal 1241 may be portable devices such as a laptop, tablet, smartphone or any other suitable device for receiving, storing, transmitting and/or displaying relevant information.

Any information described above in connection with database 1211, and any other suitable information, may be stored in memory 1215. One or more of applications 1219 may include one or more algorithms used by the mapping tool that may be used to receive historical data, determine a position of the historical data on a body part image, identify overlapping data points, assign a color and/or shape to a data point, filter data points, translate written anatomical descriptions into a point or area on a body part image and/or any other suitable tasks.

The invention may be operational with numerous other general purpose or special purpose computing system environments or configurations. Examples of well-known computing systems, environments, and/or configurations that may be suitable for use with the invention include, but are not limited to, personal computers, server computers, hand-held or laptop devices, tablets, mobile phones and/or other personal digital assistants ("PDAs"), multiprocessor systems, microprocessor-based systems, set top boxes, programmable consumer electronics, network PCs, minicomputers, mainframe computers, distributed computing environments that include any of the above systems or devices, and the like.

The invention may be described in the general context of computer-executable instructions, such as program modules, being executed by a computer. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Figure 13:
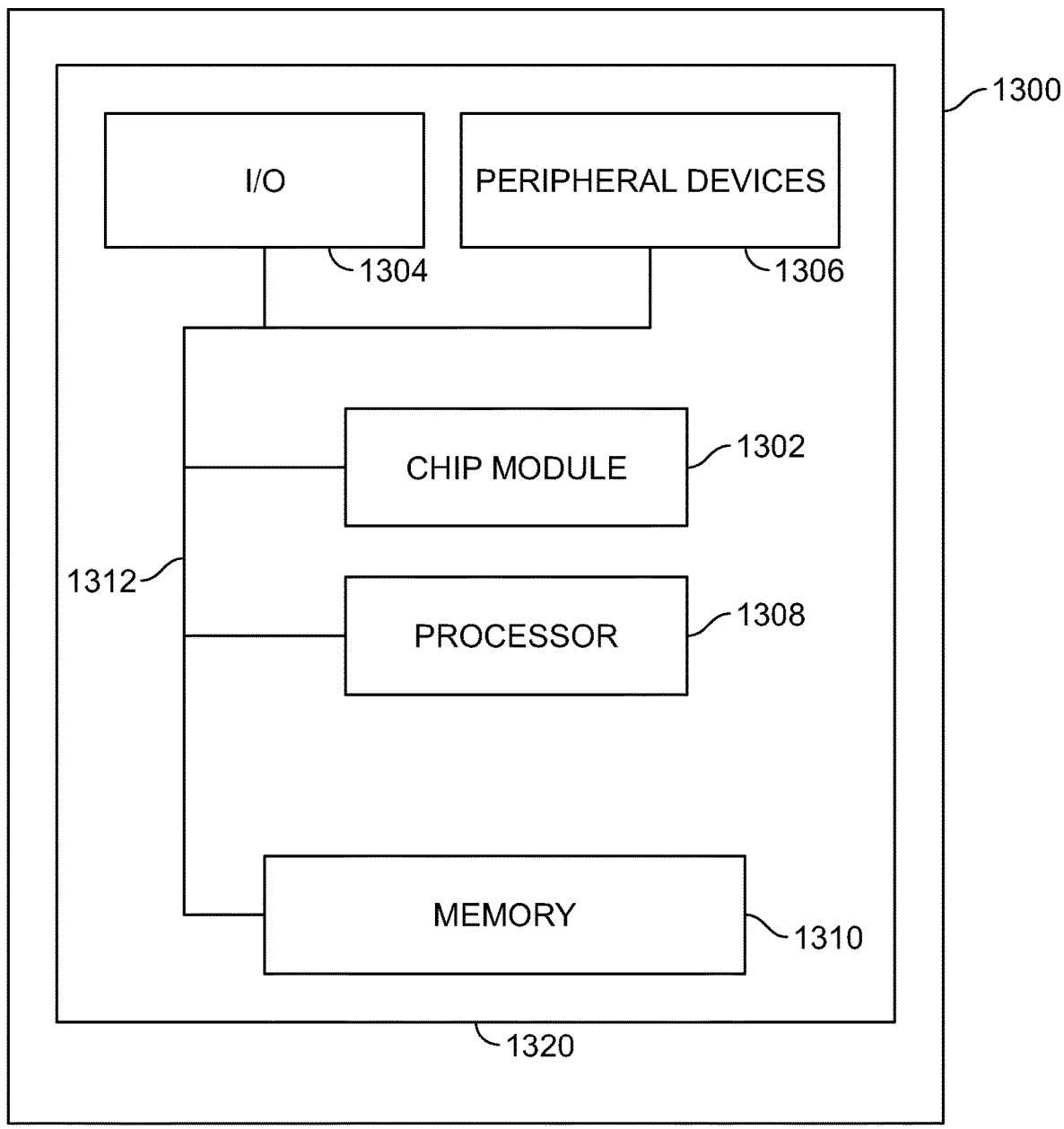
FIG. 13 shows additional illustrative computing apparatus for use with the systems and methods of the invention.
Figure 14A:
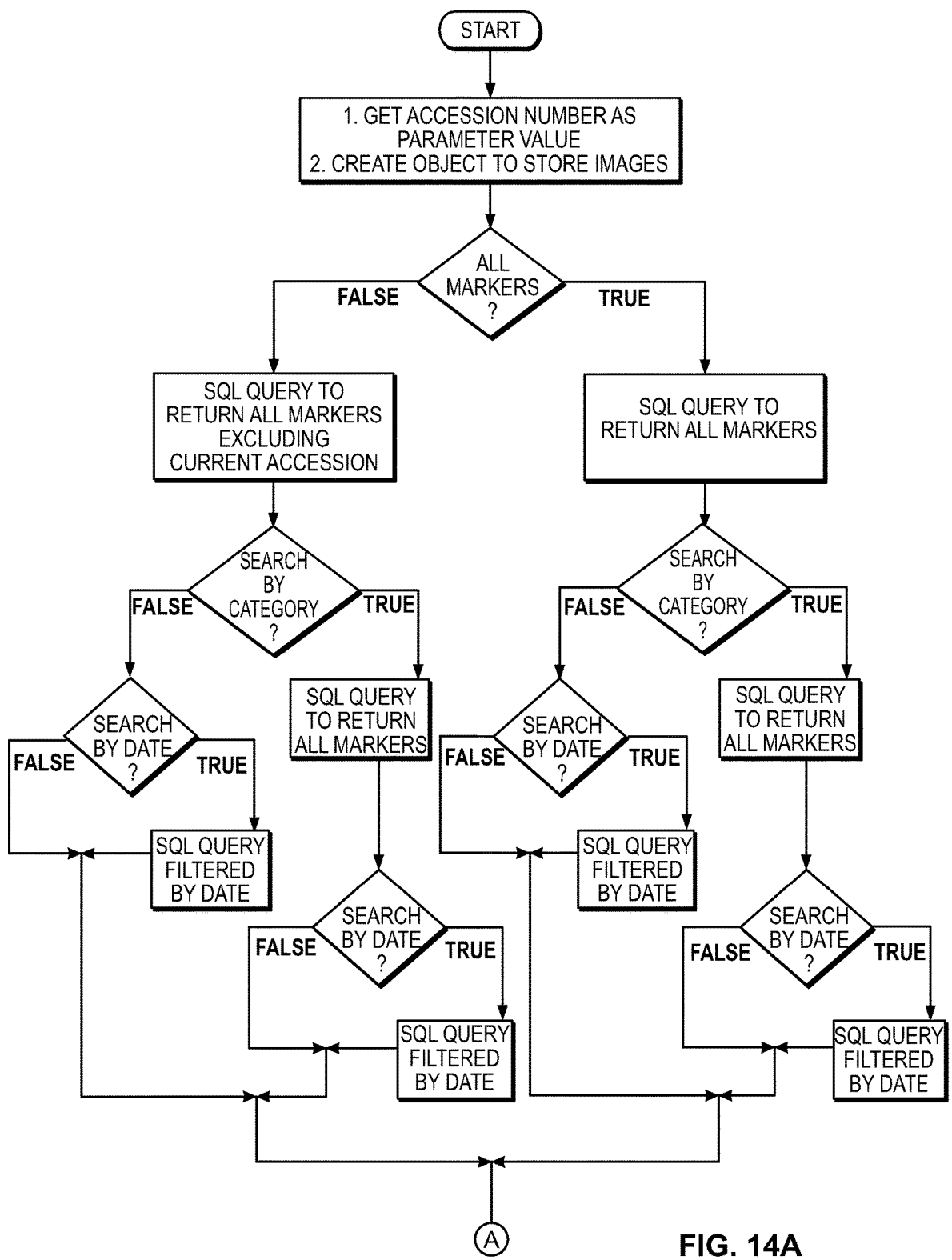
FIGS. 14A-14I shows an illustrative flowchart for use with the systems and methods of the invention.
Figure 14B:
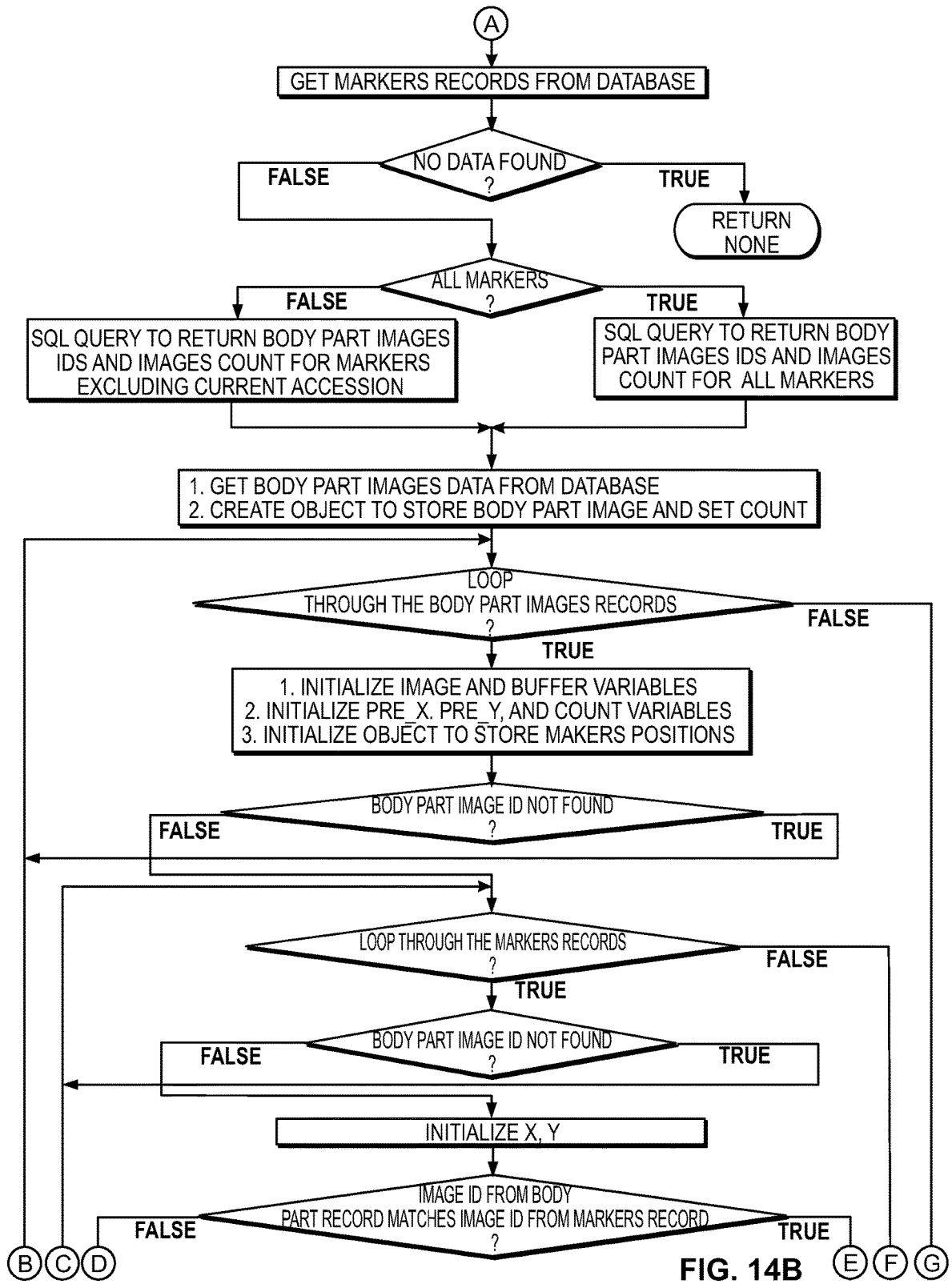
Figure 14C:
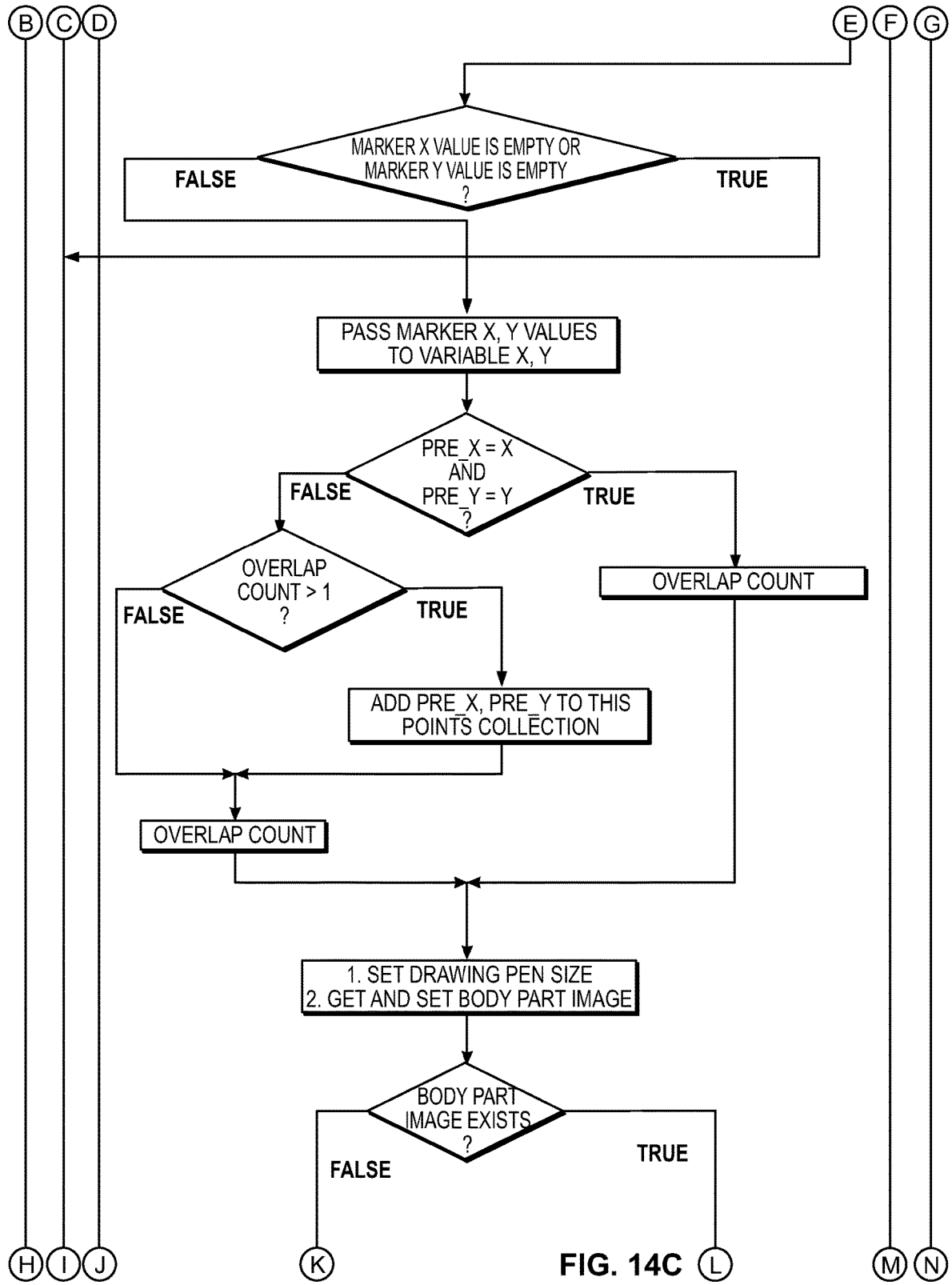
Figure 14D:
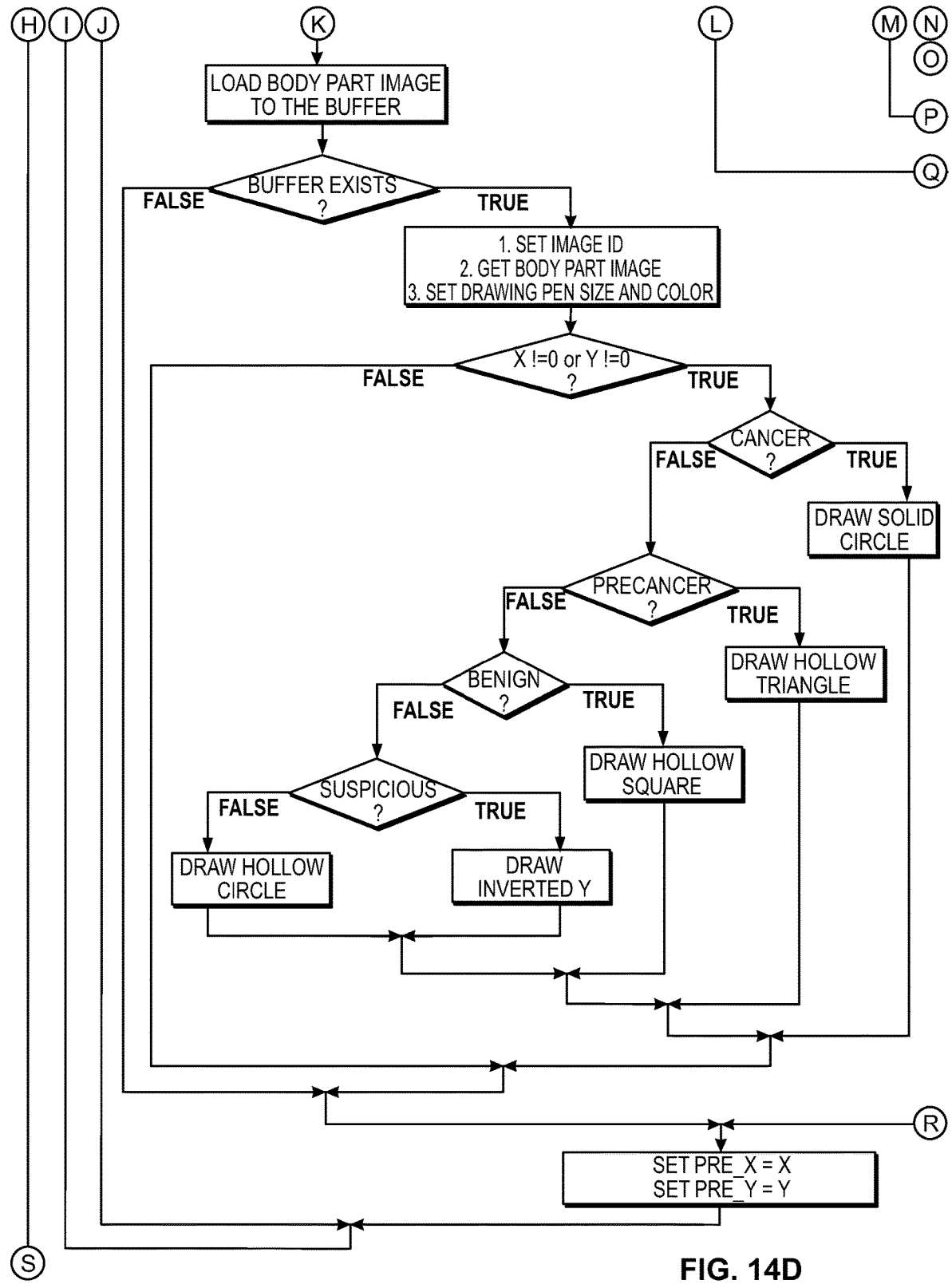
Figure 14E:
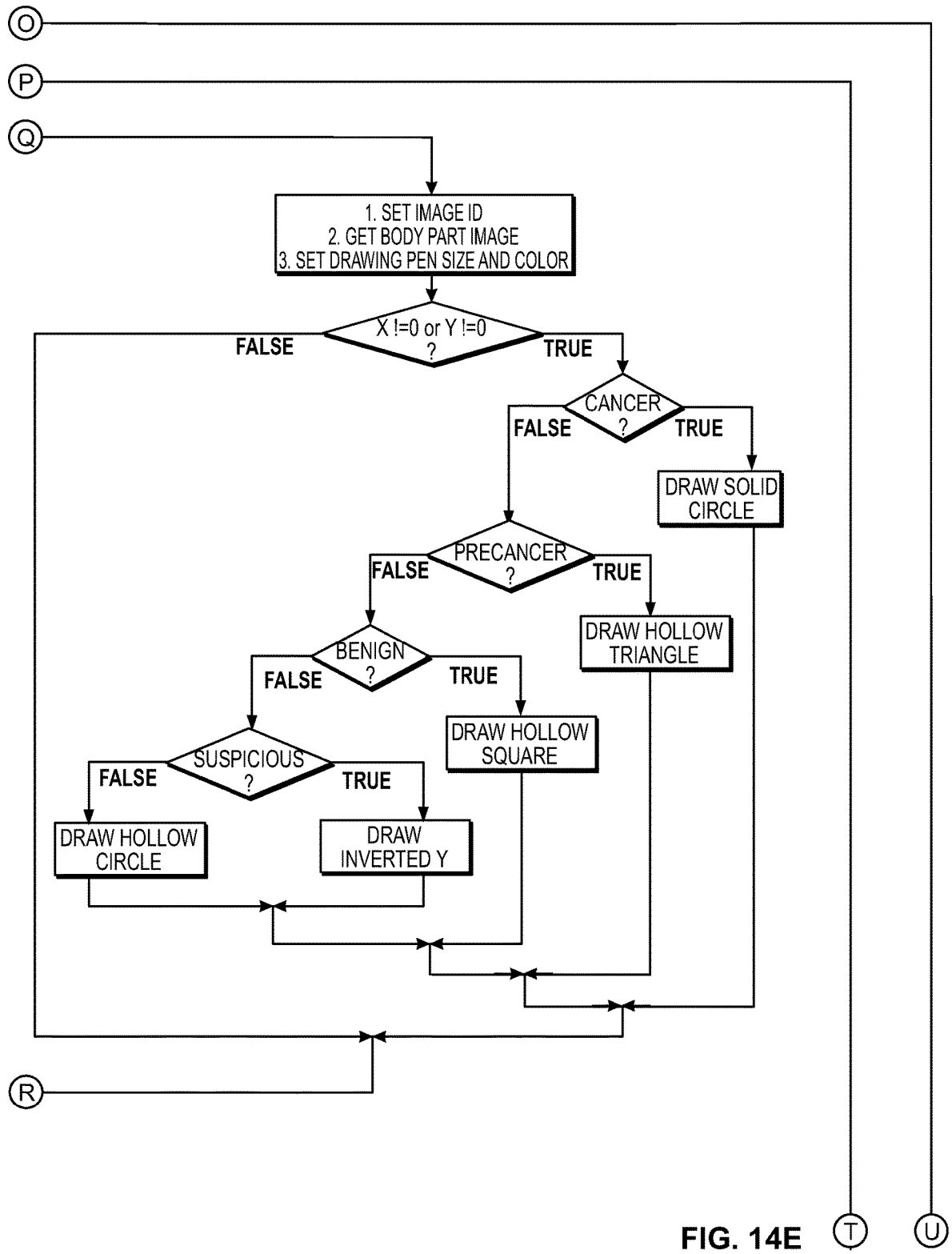
Figure 14F:
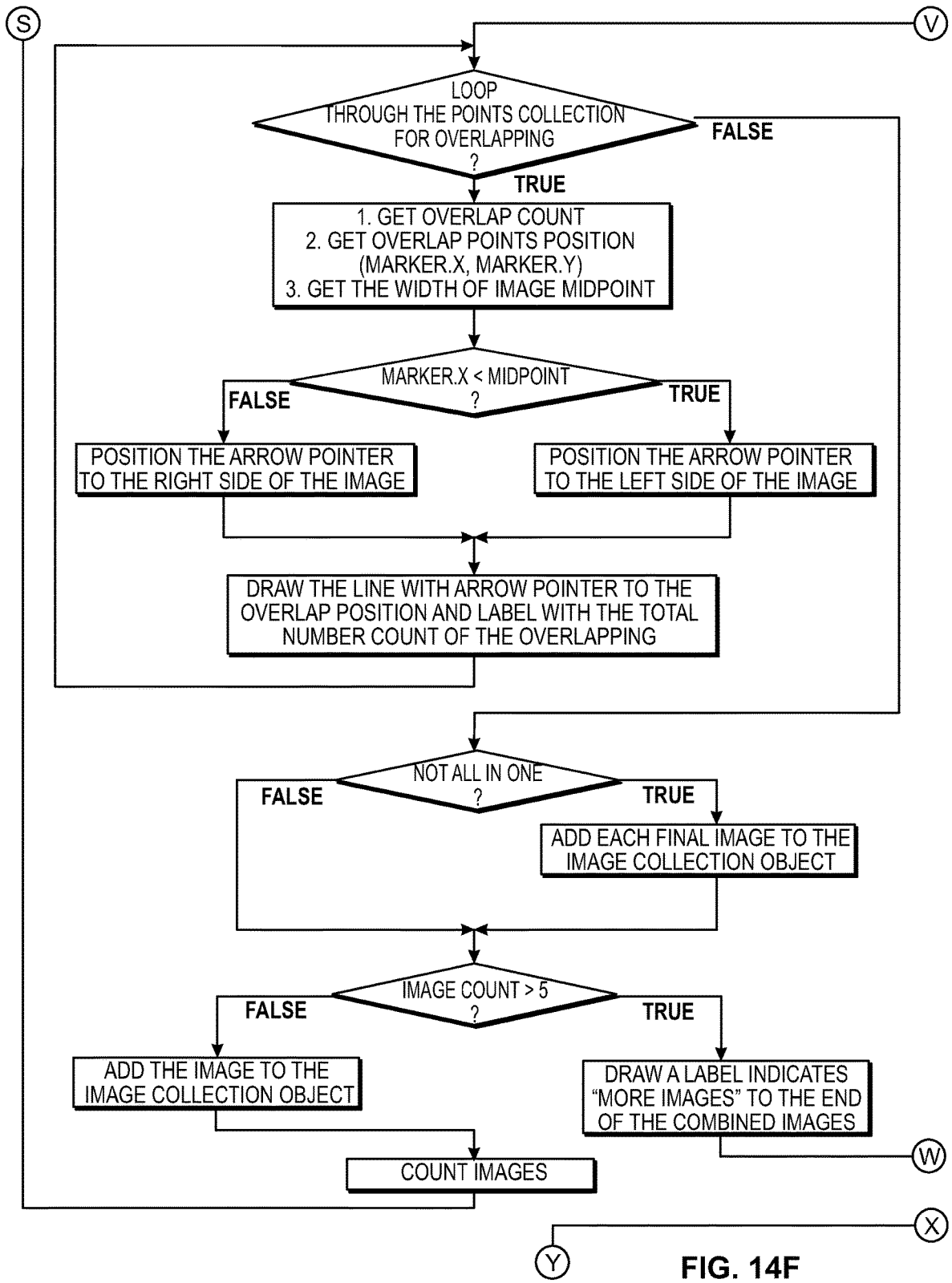
Figure 14G:
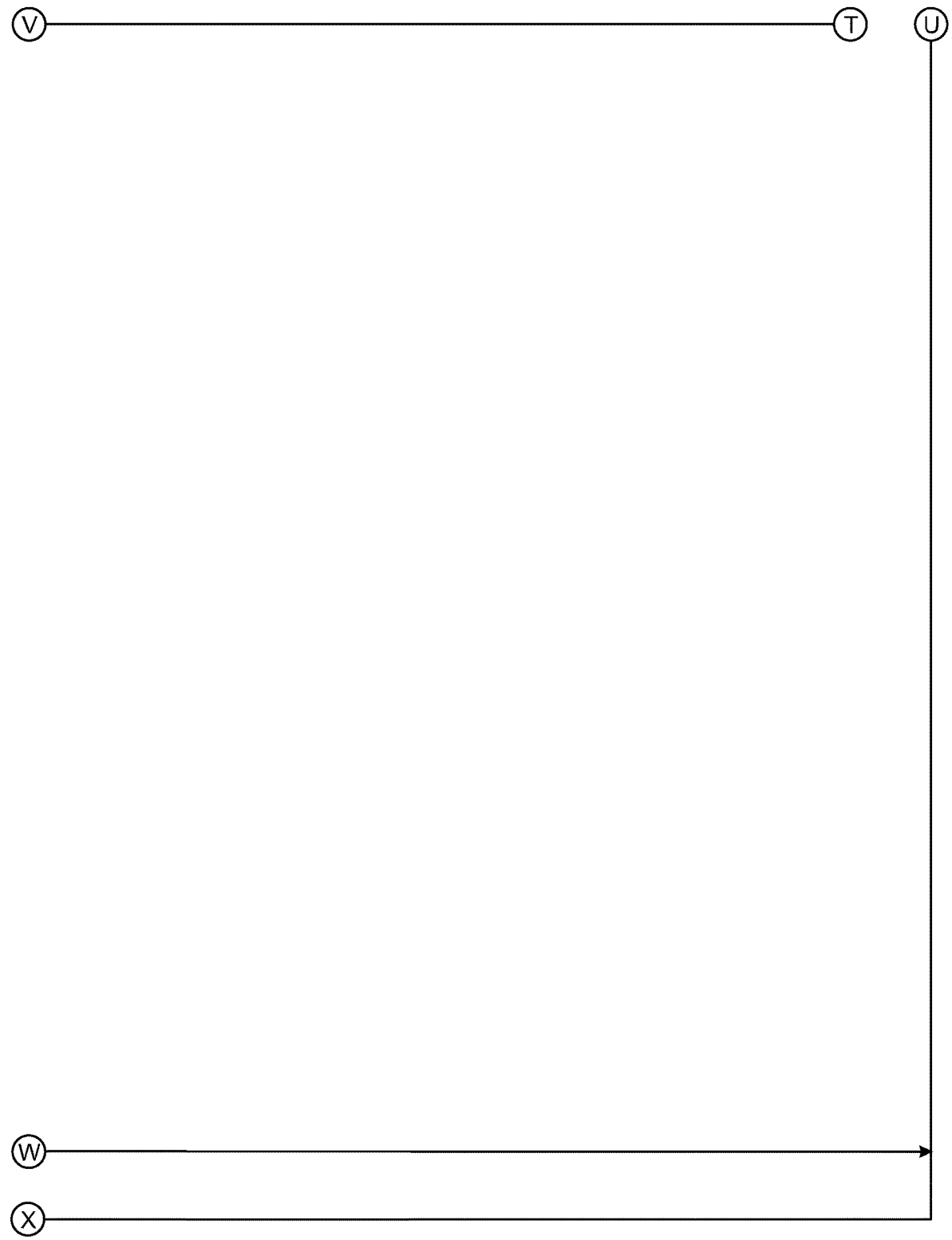
Figure 14H:
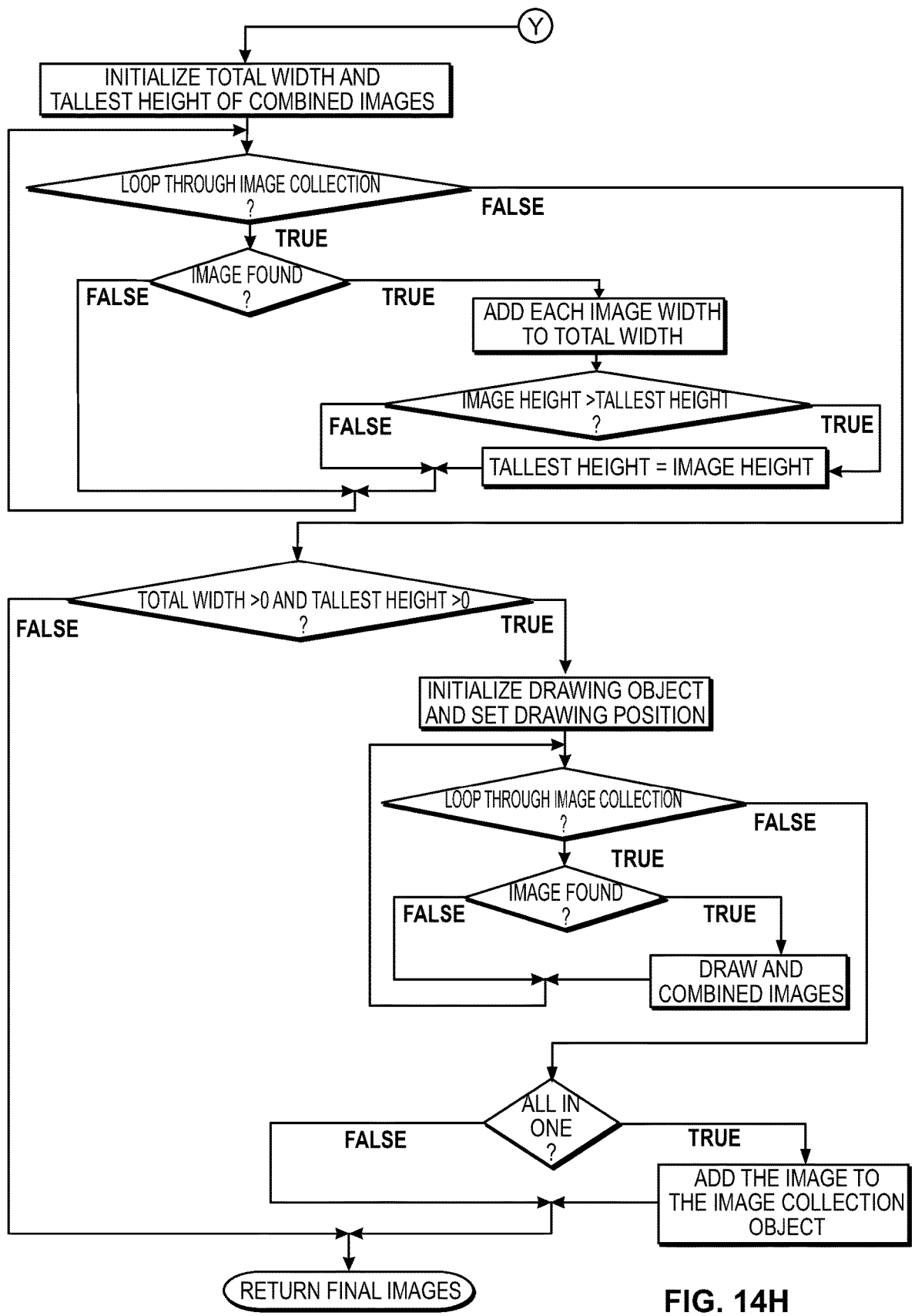
Figure 14I:
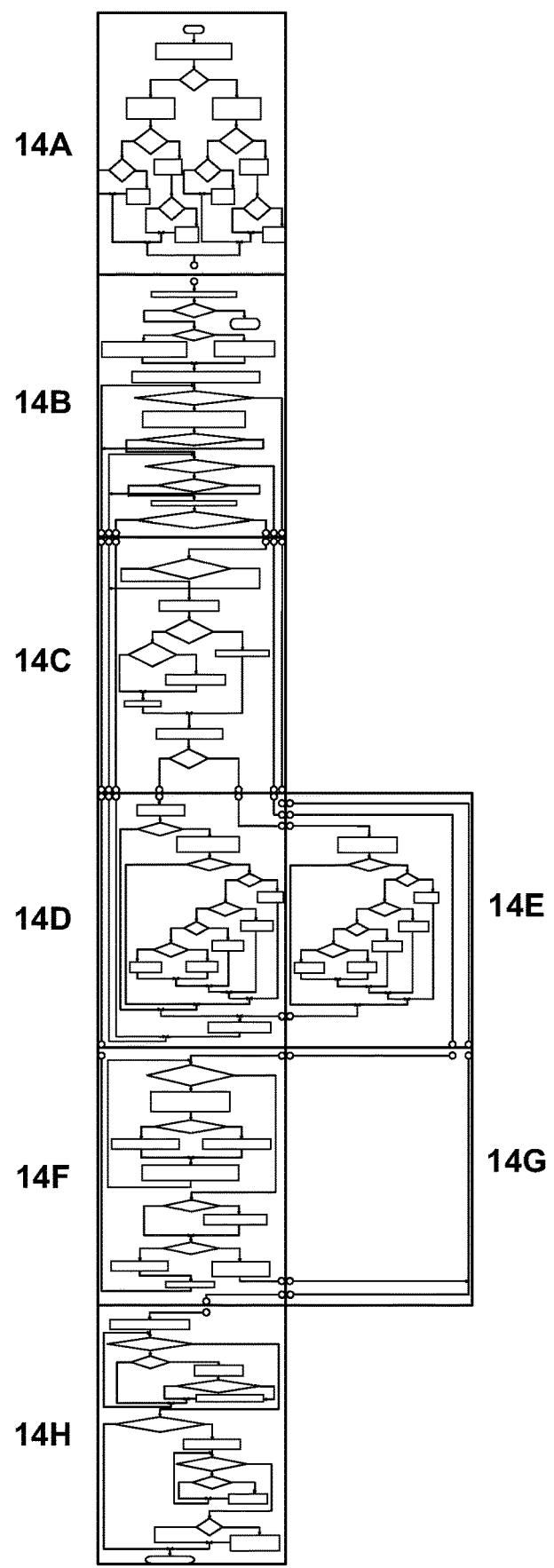

FIG. 13 shows illustrative apparatus 1300. Apparatus 1300 may be a computing machine. Apparatus 1300 may include one or more features of the apparatus shown in FIG. 13. Apparatus 1300 may include chip module 1302, which may include one or more integrated circuits, and which may include logic configured to perform any other suitable logical operations.

Apparatus 1300 may include one or more of the following components: I/O circuitry 1304, which may include a transmitter device and a receiver device and may interface with fiber optic cable, coaxial cable, telephone lines, wireless devices, PHY layer hardware, a keypad/display control device or any other suitable encoded media or devices; peripheral devices 1306, which may include counter timers, real-time timers, power-on reset generators or any other suitable peripheral devices; logical processing device 1308, which may compute data structural information, structural parameters of the data, quantify indices; and machine-readable memory 1310.

Machine-readable memory 1310 may be configured to store in machine-readable data structures: historical sequential data and any other suitable information or data structures.

Components 1302, 1304, 1306, 1308 and 1310 may be coupled together by a system bus or other interconnections 1312 and may be present on one or more circuit boards such as 1320. In some embodiments, the components may be integrated into a single chip. The chip may be silicon-based.

FIGS. 14A-14I show an illustrative algorithm for plotting historical data on a body part image and displaying the historical data overlaid on the anatomical diagram.

FIG. 14 shows illustrative process 1400. For the sake of illustration, one or more of the steps of the process illustrated in FIG. 14 will be described as being performed by a "system." The "system" may be the mapping tool, and may include one or more of the features of the apparatus, arrangements, information or processes shown in FIGS. 12-13 and/or any other suitable device or approach. The "system" may be provided by an entity. The entity may be an individual, an organization or any other suitable entity.

Process 1400 includes various steps shown in section 14A. The Steps shown in section 14A include locating patient information based on a submitted query. The patient information may be stored in a central database as part of an electronic medical record (EMR) associated with the patient. The query may include inputs such as an accession number, date range, category of diagnosis or any suitable input. The Steps shown in section 14A may parse a submitted query and identify criteria that may be used to identify desired biopsy marker records. Each biopsy marker record may correspond to a medical procedure that was performed on the patient associated with the accession number input.

Steps in section 14B include obtaining marker records requested in criteria parsed from the query. The steps in section 14B also identify body part images associated with each marker record. For example, some marker records may be associated with a patient's head. Other marker records may be associated with the patient's foot. The query may request all different marker records associated with the patient entire body over a period of time. In other examples, the query may request marker records associated with a particular organ or body part.

Each marker record may include a diagnosis code and a body location. Each body location may be associated with a body part image. For each retrieved marker record, the steps in section 14B include identifying marker records that point to identify or substantially overlapping locations on a body part image.

The steps in section 14D-14E include loading body part images associated with the retrieved marker records and plotting the diagnosis associated with each marker record. Each diagnosis may be associated with a different symbol, color or other visual indicator. A size and shape of a visual indicator may depend on the diagnosis. For example, for a diagnosis of cancer—the symbol may be larger and otherwise more prominent than if the diagnosis were benign.

The steps in section 14F may include managing the plotting of overlapping visual markers. For example, a patient may have had two or more biopsy locations (identified in two or more marker records) that are each associated with the substantially identical X,Y coordinate on a body part image. To indicate that a single location may be associated with two or more diagnoses, the steps in section 14F include drawing an arrow pointing to an overlapping location. The steps in section 14F may also include other indicators, such as text, that indicate that additional marker records have been plotted but are not currently visible. A user may need to scroll or rotate or otherwise manipulate an image to view each of the additional diagnoses associated with the two or more marker records.

The steps in section 14H include amalgamating the various body part images and plotted diagnoses. For example, a height and width of a body part image may be adjusted. Each of the body part images that include at least one plotted diagnoses may be combined to create a view of a complete human body.

The process shown in section 14I includes a high level overview of the flow of the process detailed in sections 14A-14H.

Figure 15A:
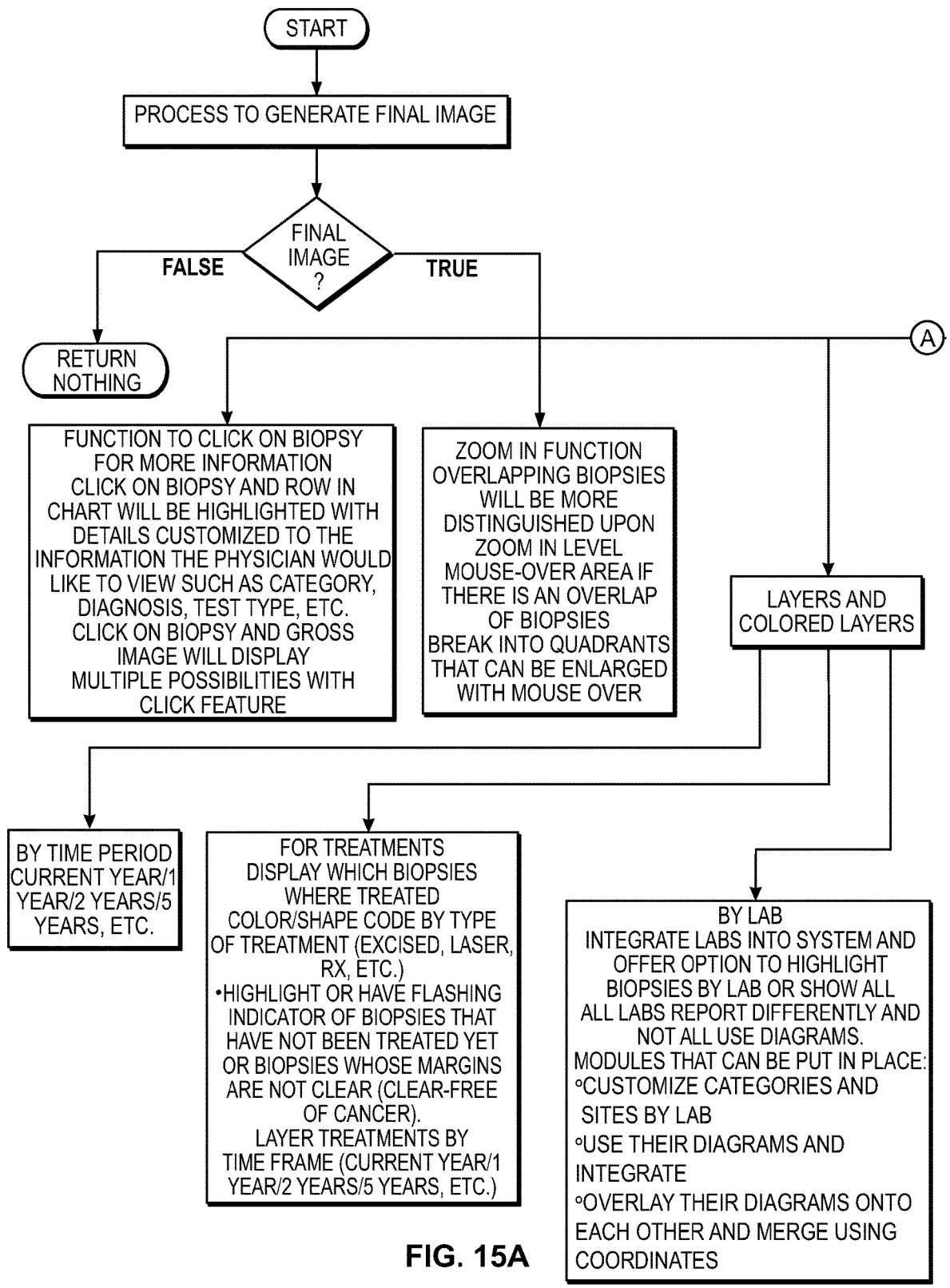
FIGS. 15A-15B shows another illustrative flowchart for use with the systems and methods of the invention.
Figure 15B:
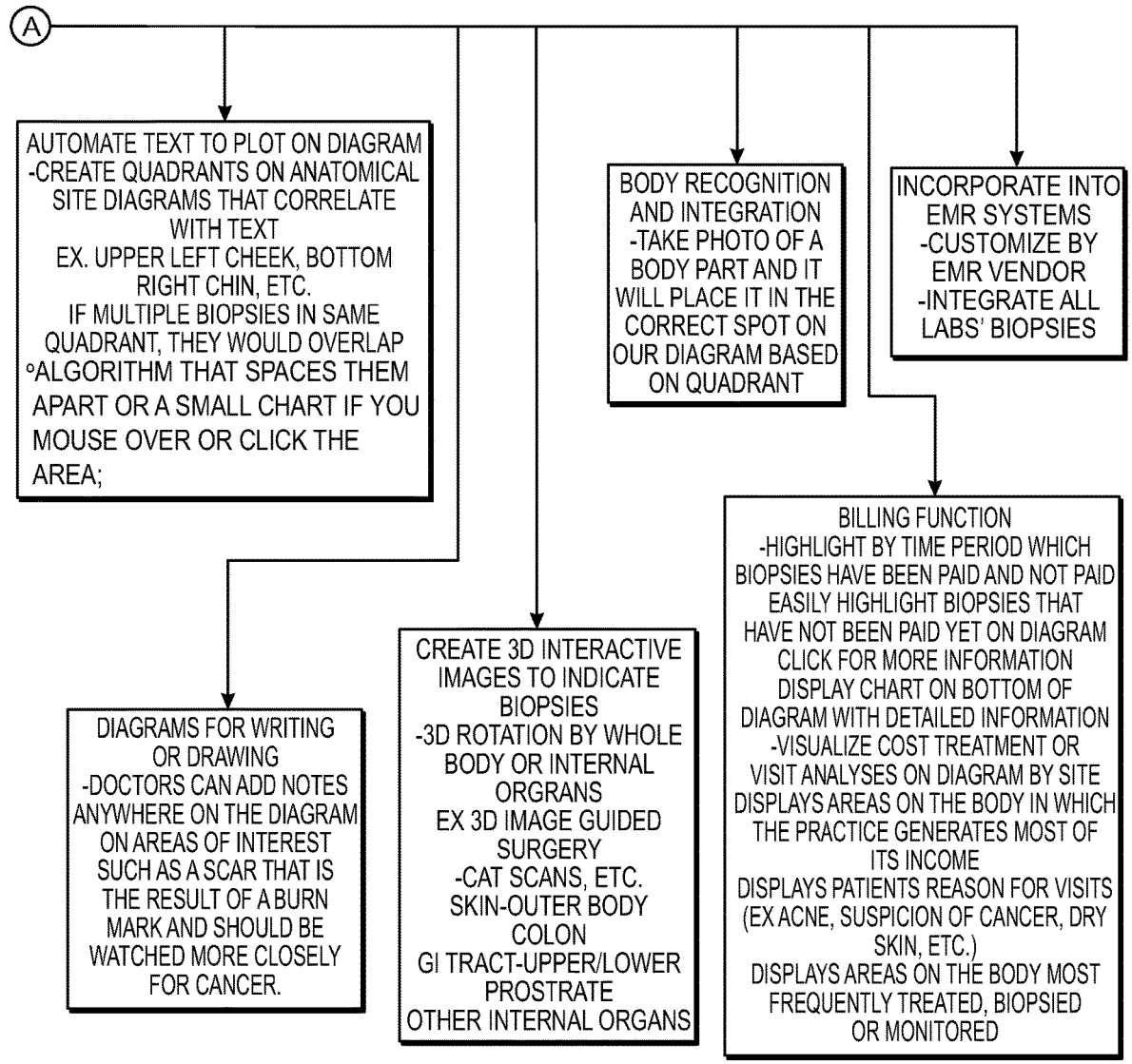

FIG. 15 shows another illustrative algorithm for plotting historical data on a body part image. The illustrative algorithm displayed in FIG. 15 may include returning a final image after completing to process the image. The final image may be generated using an algorithm detailed in FIG. 14 or any other suitable algorithm.

The final image may include one or more features or functionalities detailed in FIG. 15.

Figure 16:
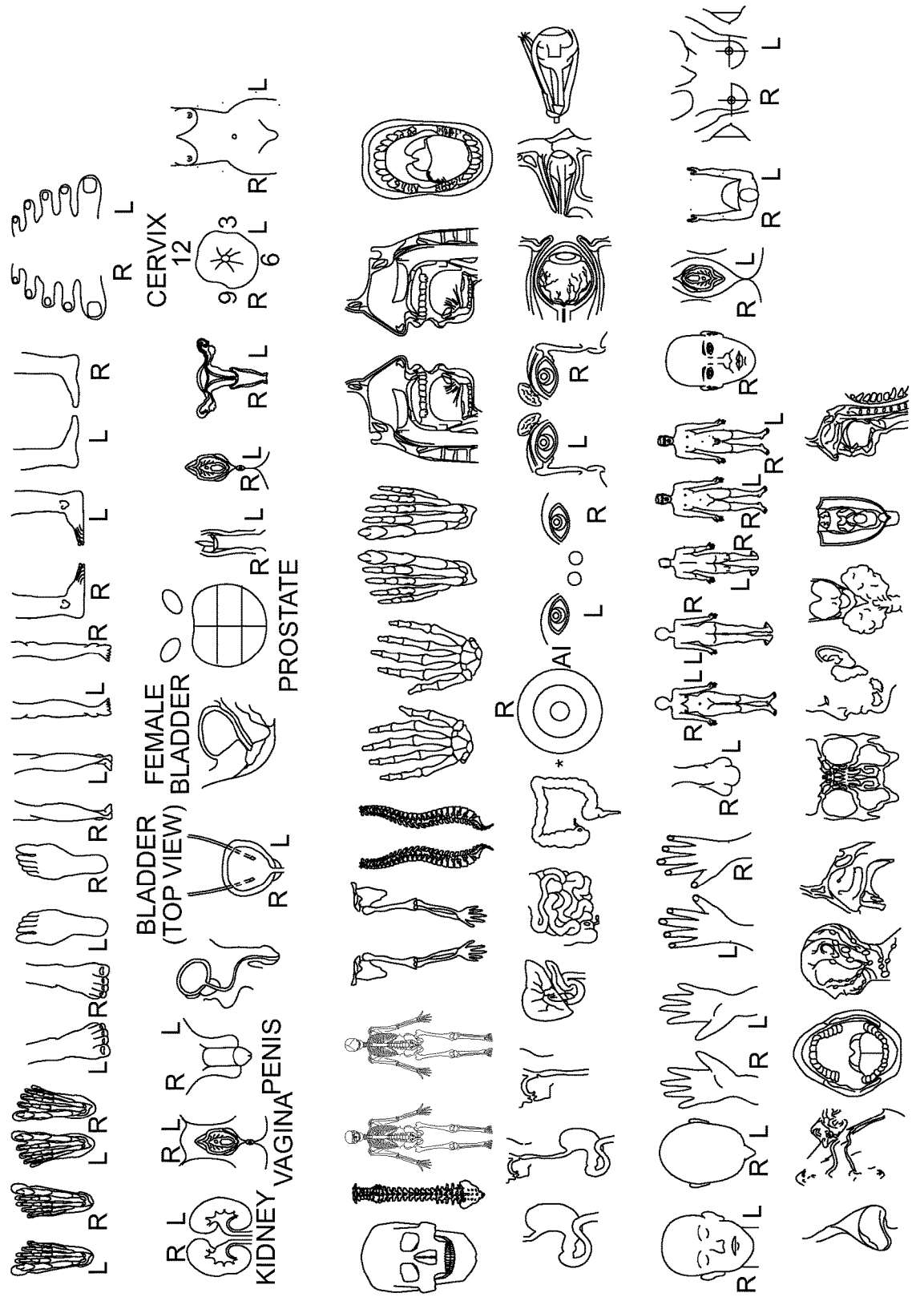
FIG. 16 shows illustrative body part images for use with the systems and methods of the invention.

FIG. 16 shows illustrative body part images that may be stored and retrieved by the mapping tool. The mapping tool may display one or more of the illustrated body part images on one or more reports in combination with one or more pieces of historical medical information.

Thus, apparatus and methods for plotting pathological diagnoses on anatomical diagrams are provided. Persons skilled in the art will appreciate that the present invention can be practiced in embodiments other than the described embodiments, which are presented for purposes of illustration rather than of limitation.

What is claimed is:

1. A computer-implemented method for extracting biopsy data from a photograph, the method comprising executing on a processor the steps of:
   receiving the photograph and a patient identifier associated with the photograph;
   correlating the photograph with a body part image;
   retrieving the body part image and match points associated with the body part image;
   identifying the match points on the photograph;
   positioning the body part image relative to the photograph using the match points;
   identifying a first biopsy location on the photograph;
   recording the first biopsy location on the body part image;
   storing the first biopsy location and a body part ID associated with the body part image in a biopsy marker record, the biopsy marker record being associated with the patient identifier; and
   generating, on a graphical user interface, a visual display of:
     the body part image;
     a first symbol identifying the first biopsy location on the body part image; and
     a second symbol identifying, on the body part image, a second biopsy location associated with the patient identifier.

2. The computer-implemented method of claim 1 wherein the photograph comprises two-dimensional image data.

3. The computer-implemented method of claim 1 wherein the photograph comprises three-dimensional image data.

4. The computer-implemented method of claim 1 wherein the photograph includes a picture of a human head and the match points include a top of a forehead, a bottom of a chin, a nose, and two sides of a mouth.

5. The computer-implemented method of claim 1 wherein the positioning includes centering the body part image over the photograph using the match points.

6. The computer-implemented method of claim 1 wherein the first biopsy location is a lesion point.

7. The computer-implemented method of claim 1 wherein the first symbol visually represents where on the human body a biopsy was taken from.

8. The computer-implemented method of claim 7 wherein the first symbol visually identifies a diagnosis associated with the biopsy.

9. The computer-implemented method of claim 1 wherein the visual display of the body part image is a three-dimensional display.

10. A computer-implemented method for extracting biopsy data from a photograph, the method comprising executing on a processor the steps of:
- receiving the photograph and a patient identifier associated with the photograph;
- correlating the photograph with a body part image;
- retrieving the body part image and match points associated with the body part image;
- based on the match points, positioning the body part image relative to the photograph;
- identifying a marking on the photograph;
- plotting the marking at a location on the body part image;
- storing the location and a body part ID associated with the body part image in a biopsy marker record, the biopsy marker record being associated with the patient identifier; and
- generating, on a graphical user interface, a visual display of:
  - the body part image; and
  - a symbol identifying the marking, the symbol being positioned on the body part image at the location.

11. The computer-implemented method of claim 10 wherein, the body part image is a first body part image and the symbol is a first symbol, the method further comprising integrating the first body part image with a second body part image to generate a third body part image, the second body part image including a second symbol, wherein, the integrating comprises:
- layering the first body part image on top of the second body part image; and
- the first symbol is selected based on a diagnosis associated with a first date and the second symbol is selected based on a diagnosis associated with a second date.

12. The computer-implemented method of claim 11 further comprising generating a hybrid photograph-image, the generating comprising positioning the second body part image on top of the photograph.

13. The computer-implemented method of claim 12 further comprising displaying a legend next to the third body part image, the legend identifying diagnoses associated with symbols displayed on the third body part image.

14. A computer-implemented method for extracting biopsy data from a patient image, the method comprising executing on a processor the steps of:
- receiving the patient image and a patient identifier associated with the image;
- correlating the patient image with a body part image;
- retrieving the body part image and match points associated with the body part image;
- based on the match points, orienting the body part image relative to the patient image;
- identifying a biopsy location on the patient image;
- mapping the biopsy location onto the body part image;
- generating a biopsy marker record, the record including a body part ID associated with the body part image, the biopsy location and a diagnosis associated with the biopsy location, wherein the biopsy marker record is associated with the patient identifier;
- searching a symbol record to identify a symbol associated with the diagnosis;
- using the biopsy marker record to generate, on a graphical user interface, a visual display of:
  - the body part image; and
  - the symbol being positioned on the body part image and identifying the biopsy location.

15. The computer-implemented method of claim 14 wherein, when the symbol is a first symbol and the biopsy marker record is a first biopsy marker record, the method further comprising using a second biopsy marker record to generate, on the graphical user interface, a visual display of a second symbol, the second symbol being positioned on the body part image and identifying a second biopsy location stored in the second biopsy marker record.

16. The computer-implemented method of claim 14 wherein the biopsy location is defined by X,Y,Z coordinates.

17. The computer-implemented method of claim 14 wherein the visual display illustrates both a front and a back of a human body part simultaneously.

18. The computer-implemented method of claim 14 wherein the body part image is generated using data from a three-dimensional image guided surgery.

19. The computer-implemented method of claim 14 wherein the body part image is generated using data from a computerized axial tomography ("CAT") scan.

20. The computer-implemented method of claim 14 wherein the patient image is a based on a magnetic renaissance imaging ("MM") scan.

21. The computer-implemented method of claim 14 wherein the patient image is a two-dimensional photograph.

* * * * *

UNITED STATES PATENT AND TRADEMARK OFFICE
CERTIFICATE OF CORRECTION

PATENT NO. : 10,546,656 B2  
APPLICATION NO. : 16/403715  
DATED : January 28, 2020  
INVENTOR(S) : Kee Chan et al.

Page 1 of 1

It is certified that error appears in the above-identified patent and that said Letters Patent is hereby corrected as shown below:

In the Claims

Claim 20, Column 26, Line 45 replace "("MM")" with --("MRI")--.

Signed and Sealed this  
Second Day of February, 2021

Drew Hirshfeld  
*Performing the Functions and Duties of the*  
*Under Secretary of Commerce for Intellectual Property and*  
*Director of the United States Patent and Trademark Office*